(12) United States Patent
Pillow et al.

(10) Patent No.: US 9,812,647 B2
(45) Date of Patent: *Nov. 7, 2017

(54) ORGANIC LIGHT-EMITTING DEVICE AND METHOD

(75) Inventors: Jonathan Pillow, Cambridgeshire (GB); Matthew Roberts, Cambridgeshire (GB); Martina Pintani, Cambridgeshire (GB); Simon King, Cambridgeshire (GB); Michael Cass, Cambridgeshire (GB)

(73) Assignees: Cambridge Display Technology, Ltd., Godmanchester (GB); Sumitomo Chemical Company Limited, Tokyo (JP)

( * ) Notice: Subject to any disclaimer, the term of this patent is extended or adjusted under 35 U.S.C. 154(b) by 1276 days.

This patent is subject to a terminal disclaimer.

(21) Appl. No.: 13/805,297

(22) PCT Filed: Jun. 24, 2011

(86) PCT No.: PCT/GB2011/000962
§ 371 (c)(1),
(2), (4) Date: Apr. 8, 2013

(87) PCT Pub. No.: WO2011/161425
PCT Pub. Date: Dec. 29, 2011

(65) Prior Publication Data
US 2013/0187146 A1    Jul. 25, 2013

(30) Foreign Application Priority Data

Jun. 25, 2010   (GB) .................. 1010741.5
Jun. 25, 2010   (GB) .................. 1010742.3
Jun. 25, 2010   (GB) .................. 1010743.1
Jun. 25, 2010   (GB) .................. 1010745.6
Jan. 31, 2011   (GB) .................. 1101642.5

(51) Int. Cl.
| | |
|---|---|
| H01L 51/54 | (2006.01) |
| C09K 11/06 | (2006.01) |
| H01L 51/00 | (2006.01) |
| C07C 13/567 | (2006.01) |
| C07C 15/18 | (2006.01) |
| C07C 15/52 | (2006.01) |
| C08G 61/02 | (2006.01) |
| C08G 61/12 | (2006.01) |
| C08L 65/00 | (2006.01) |
| H01L 51/50 | (2006.01) |
| H05B 33/14 | (2006.01) |
| H01L 51/56 | (2006.01) |

(52) U.S. Cl.
CPC ........ *H01L 51/0058* (2013.01); *C07C 13/567* (2013.01); *C07C 15/18* (2013.01); *C07C 15/52* (2013.01); *C08G 61/02* (2013.01); *C08G 61/12* (2013.01); *C08G 61/122* (2013.01); *C08L 65/00* (2013.01); *C09K 11/06* (2013.01); *H01L 51/0002* (2013.01); *H01L 51/005* (2013.01); *H01L 51/0032* (2013.01); *H01L 51/0039* (2013.01); *H01L 51/0052* (2013.01); *H01L 51/5012* (2013.01); *H01L 51/5016* (2013.01); *H01L 51/56* (2013.01); *H05B 33/14* (2013.01); *C07C 2603/18* (2017.05); *C08G 2261/148* (2013.01); *C08G 2261/1414* (2013.01); *C08G 2261/15* (2013.01); *C08G 2261/226* (2013.01); *C08G 2261/228* (2013.01); *C08G 2261/312* (2013.01); *C08G 2261/3162* (2013.01); *C08G 2261/3245* (2013.01); *C08G 2261/3422* (2013.01); *C08G 2261/5222* (2013.01); *C08G 2261/95* (2013.01); *C08L 2205/02* (2013.01); *C09K 2211/1416* (2013.01); *C09K 2211/1425* (2013.01); *C09K 2211/1433* (2013.01); *H01L 51/0043* (2013.01)

(58) Field of Classification Search
None
See application file for complete search history.

(56) References Cited

U.S. PATENT DOCUMENTS

| | | | |
|---|---|---|---|
| 3,907,904 | A | 9/1975 | Luethi |
| 4,539,507 | A | 9/1985 | VanSlyke et al. |
| 4,769,304 | A | 9/1988 | Kondo et al. |
| 4,806,444 | A | 2/1989 | Yanus et al. |
| 5,723,873 | A | 3/1998 | Yang |
| 5,998,045 | A | 12/1999 | Chen et al. |
| 6,268,695 | B1 | 7/2001 | Affinito |
| 6,353,083 | B1 | 3/2002 | Inbasekaran et al. |

(Continued)

FOREIGN PATENT DOCUMENTS

| | | |
|---|---|---|
| CN | 101016248 A | 8/2007 |
| CN | 101279888 A | 10/2008 |

(Continued)

OTHER PUBLICATIONS

Kondakov et al., Triplet annihilation exceeding spin statistical limit in highly efficient fluorescent organic light-emitting diodes. J Appl Phys. Dec. 29, 2009;106:124510.1-7.

(Continued)

*Primary Examiner* — Marie R. Yamnitzky
(74) *Attorney, Agent, or Firm* — Wolf, Greenfield & Sacks, P.C.

(57) ABSTRACT

Composition which may be useful in an organic light emitting diode, the composition having a fluorescent light-emitting polymer with light-emitting repeat units, and a triplet-accepting unit mixed with the light-emitting polymer.

17 Claims, 4 Drawing Sheets

(56) References Cited

U.S. PATENT DOCUMENTS

| | | | |
|---|---|---|---|
| 6,861,502 | B1 | 3/2005 | Towns et al. |
| 7,205,366 | B2 | 4/2007 | Jaycox et al. |
| 7,326,476 | B2 | 2/2008 | Sotoyama |
| 2001/0053842 | A1 | 12/2001 | Woo et al. |
| 2002/0048688 | A1 | 4/2002 | Fukuoka et al. |
| 2002/0185635 | A1 | 12/2002 | Doi et al. |
| 2003/0068527 | A1 | 4/2003 | Noguchi et al. |
| 2003/0082404 | A1 | 5/2003 | Sotoyama et al. |
| 2003/0088043 | A1 | 5/2003 | Huang et al. |
| 2003/0143429 | A1 | 7/2003 | Suzuki et al. |
| 2003/0165716 | A1 | 9/2003 | Samuel et al. |
| 2003/0186080 | A1* | 10/2003 | Kamatani et al. ...... C08G 61/02 428/690 |
| 2004/0137263 | A1 | 7/2004 | Burn et al. |
| 2005/0048313 | A1 | 3/2005 | Sotoyama |
| 2005/0089714 | A1 | 4/2005 | Hatwar et al. |
| 2005/0095456 | A1 | 5/2005 | Takeda |
| 2005/0096491 | A1 | 5/2005 | Hashimoto |
| 2005/0153167 | A1 | 7/2005 | Suzuki et al. |
| 2005/0164029 | A1 | 7/2005 | Burn et al. |
| 2005/0214566 | A1 | 9/2005 | Shi et al. |
| 2006/0040131 | A1 | 2/2006 | Klubek et al. |
| 2006/0051611 | A1* | 3/2006 | Brunner et al. ...... C08G 61/123 428/690 |
| 2006/0073357 | A1* | 4/2006 | Brunner et al. ...... C08G 61/123 428/690 |
| 2006/0229427 | A1 | 10/2006 | Becker et al. |
| 2006/0240565 | A1 | 10/2006 | Tang et al. |
| 2007/0145886 | A1* | 6/2007 | Aziz et al. ......... H01L 51/5012 313/504 |
| 2007/0244295 | A1 | 10/2007 | Fujita |
| 2009/0066238 | A1 | 3/2009 | Chen et al. |
| 2009/0191428 | A1 | 7/2009 | Hatwar et al. |
| 2009/0308456 | A1 | 12/2009 | Rand et al. |
| 2011/0042658 | A1 | 2/2011 | Kobayashi |
| 2011/0186828 | A1 | 8/2011 | Pillow et al. |
| 2012/0008068 | A1 | 1/2012 | Doi et al. |
| 2012/0091449 | A1 | 4/2012 | Uetani et al. |
| 2012/0112170 | A1 | 5/2012 | Jen et al. |
| 2012/0116050 | A1 | 5/2012 | Muellen et al. |
| 2013/0099223 | A1 | 4/2013 | Kobayashi |
| 2013/0146813 | A1 | 6/2013 | Oshiyama et al. |
| 2013/0187145 | A1 | 7/2013 | Pegington et al. |
| 2013/0187147 | A1 | 7/2013 | King et al. |
| 2013/0200348 | A1 | 8/2013 | Pillow et al. |
| 2013/0270535 | A1 | 10/2013 | Pillow et al. |
| 2014/0103303 | A1 | 4/2014 | Carroll |

FOREIGN PATENT DOCUMENTS

| | | |
|---|---|---|
| CN | 101624441 A | 1/2010 |
| EP | 0 707 020 A2 | 4/1996 |
| EP | 0 880 303 A1 | 11/1998 |
| EP | 0 901 176 A2 | 3/1999 |
| EP | 0 949 850 A1 | 10/1999 |
| EP | 0 842 208 B1 | 5/2000 |
| EP | 1 359 790 A2 | 11/2003 |
| EP | 1 440 959 A1 | 7/2004 |
| EP | 1 487 027 A2 | 12/2004 |
| FR | 2.151.005 A1 | 4/1973 |
| GB | 2 348 316 A1 | 9/2000 |
| GB | 2 456 788 A | 7/2009 |
| GB | 2 463 040 A | 3/2010 |
| JP | 2000-164359 A | 6/2000 |
| JP | 2006-243626 A | 9/2006 |
| JP | 2006-253221 A | 9/2006 |
| WO | WO 90/13148 A1 | 11/1990 |
| WO | WO 98/05187 A1 | 2/1998 |
| WO | WO 98/10621 A1 | 3/1998 |
| WO | WO 98/57381 A1 | 12/1998 |
| WO | WO 99/48160 A1 | 9/1999 |
| WO | WO 00/48258 A1 | 8/2000 |
| WO | WO 00/53656 A1 | 9/2000 |
| WO | WO 00/55927 A1 | 9/2000 |
| WO | WO 01/19142 A1 | 3/2001 |
| WO | WO 01/81649 A1 | 11/2001 |
| WO | WO 01/83410 A1 | 11/2001 |
| WO | WO 02/84759 A1 | 10/2002 |
| WO | WO 2005/043640 A2 | 5/2005 |
| WO | WO 2006/109083 A1 | 10/2006 |
| WO | WO 2010/013006 A2 | 2/2010 |
| WO | WO 2010/078973 A1 * | 7/2010 |

OTHER PUBLICATIONS

Office Communication dated Apr. 2, 2014 for Application No. EP 11744049.5.

Office Communication dated Nov. 20, 2014 for Application No. EP 11744049.5.

Office Communication dated Dec. 2, 2010 for Application No. GB 1010741.5.

Office Communication dated Dec. 6, 2010 for Application No. GB 1010742.3.

Office Communication dated Dec. 6, 2010 for Application No. GB 1010743.1.

Office Communication dated Dec. 7, 2010 for Application No. GB 1010745.6.

Office Communication dated Jan. 31, 2012 for Application No. GB 1101642.5.

International Search Report and Written Opinion dated Jan. 20, 2012 for Application No. PCT/GB2011/000949.

International Preliminary Report on Patentability dated Jan. 10, 2013 for Application No. PCT/GB2011/000949.

International Search Report and Written Opinion dated Sep. 27, 2011 for Application No. PCT/GB2011/000950.

International Preliminary Report on Patentability dated Jan. 10, 2013 for Application No. PCT/GB2011/000950.

International Search Report and Written Opinion dated Sep. 29, 2011 for Application No. PCT/GB2011/000961.

International Preliminary Report on Patentability dated Jan. 10, 2013 for Application No. PCT/GB2011/000961.

International Search Report and Written Opinion dated Sep. 27, 2011 for Application No. PCT/GB2011/000962.

International Preliminary Report on Patentability dated Jan. 10, 2013 for Application No. PCT/GB2011/000962.

[No Author Listed], CAS Registry No. 31927-64-7. Last accessed Apr. 9, 2015. 1 page.

Becker et al., Optimisation of polyfluorenes for light emitting applications. Synth Metals. 2002; 125: 73-80.

Bernius et al., Progress with Light-Emitting Polymers. Adv Mater. 2000;12(23):1737-50.

Brown et al., Optical spectroscopy of triplet excitons and charged excitations in poly(p-phenylenevinylene) light-emitting diodes. Chem Phys Lett. 1993;210:61-6.

Chen et al., Connector Effect in Electroluminescent Properties of Poly(p-phenylene vinylene) Derivatives Containing Triazole Chromophores. Macromol Chem Phys. 2006;207(12):1070-9.

Chen et al., White organic light-emitting devices with a bipolar transport layer between blue fluorescent and orange phosphorescent emitting layers. Appl Phys Lett. 2007; 91:023505. 3 pages.

Dhoot et al., Triplet formation and decay in conjugated polymer devices. Chem Phys Lett. 2002;360:195-201.

Ego et al., Attaching perylene dyes to polyfluorene: three simple, efficient methods for facile color tuning of light-emitting polymers. J Am Chem Soc. Jan. 15, 2003;125(2):437-43.

Kang et al., Very large electro-optic coefficients from in situ generated side-chain nonlinear optical polymers. Appl Phys Lett. 2005;87:071109.1-3.

King et al., Triplet build in and decay of isolated polyspirobifluorene chains in dilute solution. J Chem Phys. Dec. 1, 2004;121(21):10803-8.

Klärner et al., Exciton Migration and Trapping in Copolymers Based on Dialkylfluorenes. Adv Mater. 1999;11(2):115-9.

Kuo et al., High-Efficiency Poly(phenylenevinylene)-co-Fluorene Copolymers Incorporating a Triphenylamine as the End Group for White-Light-Emitting Diode Applications. J Poly Sci Part A: Poly Chem. 2007;45:4504-13.

(56) References Cited

OTHER PUBLICATIONS

Lee et al., Color tuning in polyfluorenes by copolymerization with low band gap comonomers. Synth Metals. 1999;102(1-3):1087-8.

Lee et al., Investigation of Blue Organic Light-Emitting Diodes (OLEDs) with Various Hosts. J Kor Phys Soc. 2006;49(3):1052-6.

Liu et al., Molecular Design on Highly Efficient White Electroluminescence from a Single-Polymer System with Simultaneous Blue, Green, and Red Emission. Adv Mater. 2007;19(4):531-5.

Michaelson, The work function of the elements and its periodicity. J Appl Phys. 1977;48(11):4729-33.

Mills et al., Dications of fluorenylidenes. Relationship between electrochemical oxidation potentials and antiaromaticity in diphenyl-substituted fluorenyl cations. J Org Chem. Apr. 5, 2002;67(7):2003-12.

Niu et al., Thermal annealing below the glass transition temperature: A general way to increase performance of light-emitting diodes based on copolyfluorenes. Appl Phys Lett. 2002;81(4):634-6.

Peng et al., Study on the energy transfer and luminescent properties in PVK: DBVP blend system. Acta Phys Sin. 2006;55(10):5495-8.

Popovic et al., Delayed Electroluminescence in Small Molecule Based Organic Light Emitting Diodes—Evidence for Triplet-Triplet Annihilation and Recombination Center Mediated Light Generation Mechanism. J App Phys. 2005;98:013510.1-5.

Rothe et al., Triplet exciton state and related phenomena in the beta-phase of poly(9,9-dioctyl)florene. Phys Rev B. 2004;70:195213.1-5.

Setayesh et al., Bridging the Gap between Polyfluorene and Ladder-Poly-p-phenylene: Synthesis and Characterization of Poly-2,8-indenofluorene. Macromolecules. 2000;33(6):2016-20.

Shi et al., Anthanthrene Derivatives for Stable Blue-Emitting Organic Electroluminescent Devices. SID 05 Digest. 2005;36:1760-3.

Staroske et al., Single-step triplet-triplet annihilation: an intrinsic limit for the high brightness efficiency of phosphorescent organic light emitting diodes. Phys Rev Lett. May 11, 2007;98(19):197402. 1-4. Epub May 10, 2007.

Thirunavukkarasu et al., One-Pot Synthesis of Diarylmethylidenefluorenes and Phenanthrenes by Palladium-Catalyzed Multiple C[BOND]H Bond Functionalization. Chem-Eur J. 2010;16(5):1436-40.

Tokito et al., Metal oxides as a hole-injecting layer for an organic electroluminescent device. J Phys D: Appl Phys. 1996;29(11):2750-3.

Wohlgenannt et al., Photophysics properties of blue-emitting polymers. Synth Met. 2002;125:55-63.

Yamamoto, Electrically Conducting and Thermally Stable $\pi$—Conjugated Poly(arylene)s Prepared by Organometallic Processes. Prog Poly Sci. 1993;17:1153-205.

Yang et al., Efficient blue polymer light-emitting diodes from a series of soluble poly(paraphenylene)s. J Appl Phys. 1996;79:934-9.

Yang et al., Efficient polymer light emitting diodes with metal flouride/Al cathodes. Appl Phys Lett. Jul. 30, 2001;79(5):563-5.

Bernius et al., Developmental Progress of Electroluminescent Polymeric Materials and Devices. SPIE. 1999;3797:129-37.

\* cited by examiner

ORGANIC LIGHT-EMITTING DEVICE AND METHOD

RELATED APPLICATIONS

The present application is a national stage filing under 35 U.S.C. §371 of international PCT application, PCT/GB2011/000962, filed Jun. 24, 2011, which claims priority to United Kingdom patent application, GB 1010741.5, filed Jun. 25, 2010, United Kingdom patent application. GB 1010742.3, filed Jun. 25, 2010, United Kingdom patent application, GB 1010743.1, filed Jun. 25, 2010, United Kingdom patent application, GB 1010745.6, filed Jun. 25, 2010, and United Kingdom patent application, GB 1101642.5, filed Jan. 31, 2011, each of which is incorporated herein by reference.

SUMMARY OF THE INVENTION

This invention relates to organic light emitting compositions, devices containing the same, and methods of making said devices.

BACKGROUND OF THE INVENTION

Electronic devices comprising active organic materials are attracting increasing attention for use in devices such as organic light emitting diodes, organic photovoltaic devices, organic photosensors, organic transistors and memory array devices. Devices comprising organic materials offer benefits such as low weight, low power consumption and flexibility. Moreover, use of soluble organic materials allows use of solution processing in device manufacture, for example inkjet printing or spin-coating.

A typical organic light-emissive device ("OLED") is fabricated on a glass or plastic substrate coated with a transparent anode such as indium-tin-oxide ("ITO"). A layer of a thin film of at least one electroluminescent organic material is provided over the first electrode. Finally, a cathode is provided over the layer of electroluminescent organic material. Charge transporting, charge injecting or charge blocking layers may be provided between the anode and the electroluminescent layer and/or between the cathode and the electroluminescent layer.

In operation, holes are injected into the device through the anode and electrons are injected into the device through the cathode. The holes and electrons combine in the organic electroluminescent layer to form excitons which then undergo radiative decay to give light.

In WO90/13148 the organic light-emissive material is a conjugated polymer such as poly(phenylenevinylene). In U.S. Pat. No. 4,539,507 the organic light-emissive material is of the class known as small molecule materials, such as tris-(8-hydroxyquinoline)aluminium ("Alq$_3$"). These materials electroluminesce by radiative decay of singlet excitons (fluorescence) however spin statistics dictate that up to 75% of excitons are triplet excitons which undergo non-radiative decay, i.e. quantum efficiency may be as low as 25% for fluorescent OLEDs-see, for example, Chem. Phys. Lett., 1993, 210, 61, Nature (London), 2001, 409, 494, Synth. Met., 2002, 125, 55 and references therein.

It has been postulated that the presence of triplet excitons, which may have relatively long-lived triplet excited states, can be detrimental to OLED lifetime as a result of triplet-triplet or triplet-singlet interactions ("lifetime" as used herein in the context of OLED lifetime means the length of time taken for the luminance of the OLED at constant current to fall by 50% from an initial luminance value, and "lifetime" as used herein in the context of lifetime of a triplet excited state means the half-life of a triplet exciton).

WO 2005/043640 discloses that blending a perylene derivative with an organic light-emissive material in an organic light-emissive device can give a small increase in the lifetime of the device. However, while higher concentrations of perylene derivative give greater improvements in lifetime this results in a significant red-shift in the emission spectrum.

US 2007/145886 discloses an OLED comprising a triplet-quenching material to prevent or reduce triplet-triplet or triplet-singlet interactions.

US 2005/095456 discloses an OLED having a light-emitting layer comprising a host material, a dye or pigment and an additive exhibiting an absorption edge of which energy level is higher than that of an absorption edge of the dye or the pigment.

OLEDs have great potential for display and lighting applications. However, there remains a need to improve performance of these devices.

SUMMARY OF THE INVENTION

In a first aspect the invention provides a composition comprising a fluorescent light-emitting polymer and a triplet-accepting unit.

In one optional arrangement, the triplet-accepting unit is a triplet accepting compound mixed with the light emitting polymer and any other component or components of the composition.

In another optional arrangement, the triplet-accepting unit is bound to the light-emitting polymer or to any other component or components of the composition.

Optionally, the composition comprises at least one of a hole transporting material and an electron transporting material and wherein the triplet-accepting unit is bound to at least one of the hole transporting material, the electron transport-ing material and the light-emitting polymer.

Optionally, the triplet-accepting unit is bound to the light emitting polymer.

Optionally, the light-emitting polymer comprises a light-emitting repeat unit and at least one of repeat units providing electron transport and repeat units providing hole transport, wherein the triplet-accepting material is bound to at least one of the light-emitting repeat unit, the repeat unit providing electron transport and the repeat unit providing hole transport.

Optionally, the triplet-accepting unit is a repeat unit in the main chain of the light-emitting polymer or a side-group or end-group of the light-emitting polymer.

Optionally, the triplet-accepting unit is substituted with one or more solubilising groups.

Optionally, the solubilising group is selected from alkyl and alkoxy.

Optionally, the light-emitting polymer comprises arylamine repeat units.

Optionally, the arylamine repeat units are units of formula (V):

wherein $Ar^1$ and $Ar^2$ are optionally substituted aryl or heteroaryl groups, n is greater than or equal to 1, preferably 1 or 2, and R is H or a substituent.

Optionally, the polymer comprises aryl or heteroaryl repeat units.

Optionally, the polymer comprises repeat units of formula (IV):

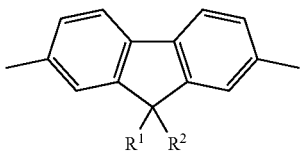

(IV)

wherein $R^1$ and $R^2$ are independently H or a substituent, and $R^1$ and $R^2$ may be linked to form a ring.

Optionally, the triplet-accepting material is present in an amount of at least 0.1 mol %.

Optionally, the composition has a photoluminescent light emission peak wavelength in the range of 400 to 500 nm.

Optionally, the triplet-accepting unit does not comprise a perylene.

In a second aspect the invention provides a formulation comprising a solvent and a composition according to the first aspect.

In a third aspect the invention provides an organic light-emitting device comprising an anode, a cathode and a light-emitting layer between the anode and cathode, wherein the light-emitting layer comprises a composition according to the first aspect.

In a fourth aspect the invention provides a method of forming an organic light-emitting device according to the third aspect, the method comprising the steps of depositing the formulation according to the second aspect and evaporating the solvent.

In a fifth aspect the invention provides use of a unit for acceptance of triplet excitons generated by a light-emitting polymer in a composition comprising the triplet-accepting unit and the light-emitting polymer.

The triplet-accepting unit and light-emitting polymer may be as described with reference to the first aspect of the invention.

Optionally according to the fifth aspect, the triplet-accepting unit is physically mixed with the light-emitting polymer.

Optionally according to the fifth aspect, the triplet-accepting unit is chemically bound to the light-emitting polymer.

Optionally according to the fifth aspect, the triplet-accepting unit quenches triplet excitons generated by the light-emitting polymer.

Optionally according to the fifth aspect, the triplet accepting unit mediates triplet-triplet annihilation of triplet excitons transferred from the light emitting polymer to the triplet-accepting unit.

It will be appreciated that the invention in its first aspect relates to a composition wherein the triplet-accepting unit emits substantially no light. The excited singlet state energy level ($S_1$) of the light-emitting polymer is no higher than, and preferably lower than, the corresponding energy level of triplet-accepting unit in order to prevent any substantial transfer of singlet excitons from the $S_1$ energy level of the light-emitting polymer to the $S_1$ level of the triplet-accepting material.

"Triplet accepting unit" as used herein means a unit capable of receiving triplet excitons from the light emitting polymer. In order to function efficiently, the triplet accepting unit has a triplet excited state energy level $T_1$ that is lower in energy than that of the light-emitting unit.

DETAILED DESCRIPTION OF THE INVENTION

The present inventors have identified a number of pathways by which triplet excitons may be caused to undergo decay in order to reduce or eliminate decay by pathways that cause a drop in device lifetime. This includes pathways in which triplet excitons decay non-radiatively by a quenching process and pathways in which triplet excitons undergo triplet-triplet annihilation, resulting in delayed fluorescence that can provide for better device efficiency as compared to non-radiative quenching pathways.

Triplet Quenching

Figure 1:
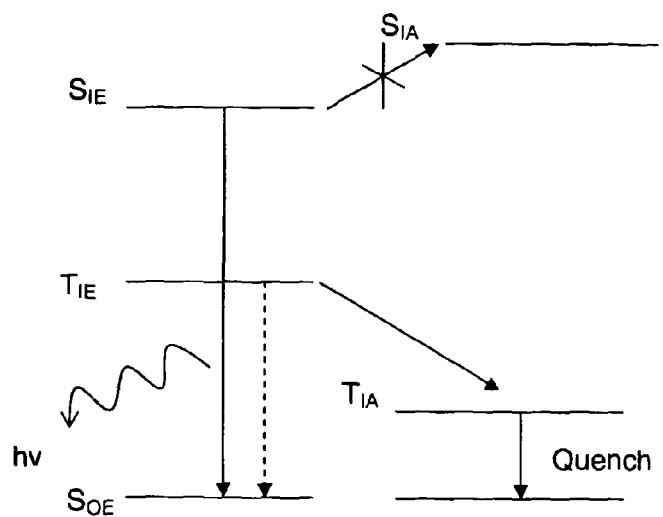
FIG. 1 is a schematic illustration of triplet quenching.

FIG. 1 illustrates a first energy transfer mechanism for an exemplary OLED. For the avoidance of any doubt energy level diagrams herein, including FIG. 1, are not drawn to any scale. FIG. 1 illustrates energy transfer for an OLED provided with a light emitting polymer having a singlet excited state energy level $S_{1E}$ and a singlet ground state energy level $S_{0E}$. Singlet excitons having energy $S_{1E}$ decay by emission of fluorescent light hv, illustrated by the solid arrow between $S_{1E}$ and $S_{0E}$ in FIG. 1. Triplet-triplet exciton interactions or triplet-singlet exciton interactions may create "super-excited" states on the light-emitting polymer. Without wishing to be bound by any theory, it is believed that formation of these highly energetic "super-excited" states on the light emitting polymer may be detrimental to operational lifetime of the polymer. However, by providing a triplet accepting unit having an excited triplet state energy level $T_{1A}$ that is lower than $T_{1E}$, it is possible for triplet excitons to be transferred for quenching to the triplet accepting unit, the alternative of radiative decay from $T_{1E}$ to $S_{0E}$, illustrated by a dotted line in FIG. 1, being a spin-forbidden process. $S_1$ and $T_1$ levels can be measured from the fluorescence and phosphorescence spectra respectively.

The triplet accepting unit of this example has a singlet excited state energy level $S_{1A}$ that is higher than the singlet excited state energy level $S_{1E}$ in order to substantially or completely prevent transfer of singlet excitons from $S_{1E}$ to $S_{1A}$. Preferably, $S_{1A}$ is at least kT higher in energy than $S_{1E}$ in order to prevent any substantial back-transfer of excitons. Likewise, $T_{1E}$ is preferably at least kT higher in energy than $T_{1A}$. Although it may be preferable for energy level $S_{1A}$ to be greater than $S_{1E}$, it will be appreciated that this is not essential in order for triplet absorption to occur.

Triplet-Triplet Annihilation

Figure 2:
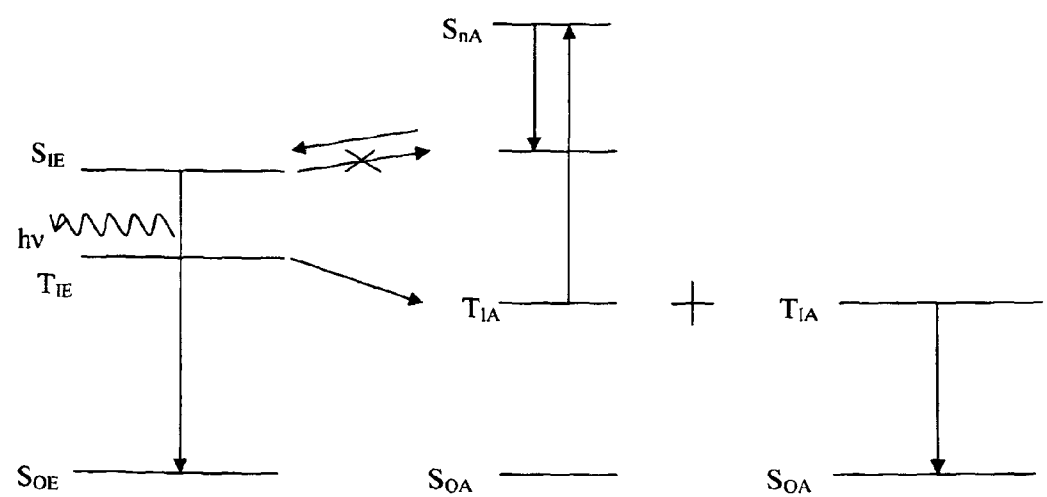
FIG. 2 is a schematic illustration of a first triplet-triplet annihilation mechanism.

FIG. 2 illustrates a second energy transfer mechanism for an exemplary OLED.

According to this embodiment, triplet-triplet annihilation (TTA), caused by an interaction between two triplet-accepting units, results in a triplet-triplet annihilated singlet exciton having an energy of up to $2 \times T_{1A}$, wherein $T_{1A}$ represents the triplet excited state energy level of the triplet-accepting material. This singlet exciton, formed on a first of the two triplet-accepting units, has energy level $S_{nA}$ that is higher in energy than $S_{1A}$ and $S_{1E}$ and so it may transfer to $S_{1A}$ and then to $S_{1E}$ from which light hv may be emitted as delayed fluorescence. The triplet exciton on the second of the two triplet-accepting units may decay to the ground state $T_{0A}$.

Initially, the triplet exciton formed at $T_{1E}$ is transferred to $T_{1A}$. By providing a triplet-accepting material having energy level $T_{1A}$ that is lower than $T_{1E}$, rapid transfer of excitons from $T_{1E}$ to $T_{1A}$ may occur. This transfer is relatively rapid compared to the rate of decay of triplet excitons from $T_{1E}$ to $S_{0E}$, illustrated by a dotted arrow in FIG. 1, which is a spin-forbidden process. The energy gap between $T_{1E}$ and $T_{1A}$ is preferably greater than kT in order to avoid back-transfer of excitons from $T_{1A}$ to $T_{1E}$. Likewise, the energy gap between $S_{1A}$ and $S_{1E}$ is preferably greater than kT in order to avoid back-transfer of excitons from $S_{1E}$ to $S_{1A}$.

A pathway for decay of the triplet exciton on $T_{1A}$ in competition with triplet-triplet annihilation is the non-radiative (quenching) pathway to $S_{0A}$ described above with reference to FIG. 1. A number of measures may be taken to maximise the probability of TTA rather than decay to $S_{0A}$, in particular:

i) The triplet-absorbing material may be selected such that triplet excitons on $T_{1A}$ have a relatively long lifetime $\tau_{T4}$. A relatively long lifetime not only means that the rate of decay to $S_{0A}$ is relatively slow but also that the likelihood of TTA is relatively high.

ii) The concentration of triplet-absorbing material in the light-emitting layer may be relatively high, for example greater than 1 mol %, for example in the range of 1-10 mol %.

iii) Two or more triplet-accepting materials may be provided in close proximity, for example as described below with reference to units of formula (II).

Each of these measures may be used alone or in combination.

Figure 3:
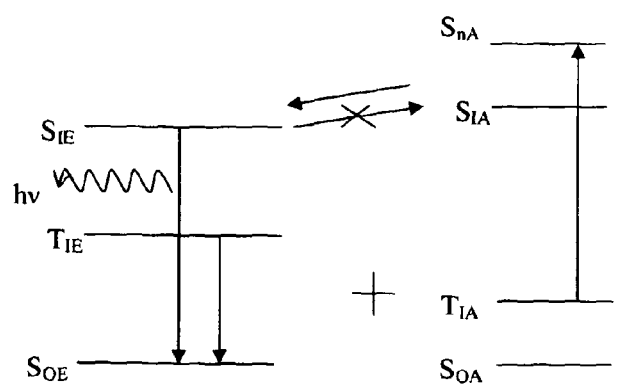
FIG. 3 illustrates a second triplet-triplet annihilation mechanism.

FIG. 3 illustrates a third energy transfer mechanism for an exemplary OLED.

In this case, triplet-triplet annihilation occurs between the triplet exciton of energy $T_{1A}$ located on the triplet accepting triplet-accepting unit and the triplet exciton of energy $T_{1E}$ located on the light-emitting polymer. It will be appreciated that this results in a triplet-triplet annihilated singlet exciton (TTAS) having an energy of up to $T_{1E}+T_{1A}$. This singlet exciton's energy level of $S_{nA}$ is higher in than that of $S_{1E}$ and so it may transfer its energy to $S_{1A}$ and from there to $S_{1E}$ from which light hv may be emitted as delayed fluorescence.

In FIGS. 2 and 3, although it may be preferable for energy level $S_{1A}$ to be greater than $S_{1E}$, it will be appreciated that this is not essential in order for triplet absorption to occur.

Without wishing to be bound by any theory, it is believed that avoiding formation of super-excited states on the light-emitting polymer formed during OLED driving may improve device lifetime. Moreover, by utilising a triplet accepting unit to generate TTA to produce stable delayed fluorescence it is possible to improve efficiency as compared to a device in which triplet excitons are quenched (as illustrated in FIG. 1) or as compared to a device in which there is no triplet accepting unit wherein intensity of delayed fluorescence may drop sharply following initial OLED driving.

It will be appreciated that it is possible for two or all three of the triplet-quenching mechanism and the two TTA mechanisms described above to occur within the same device, and that the amount of delayed fluorescence from each of the TTA two mechanisms will depend on factors such as the concentration of light emitting material, the concentration of triplet accepting units and the excited state lifetime of triplet excitons on the light emitting unit and the triplet accepting unit. Measures described above with reference to FIG. 2 may be employed to increase the probability of TTA.

The rate constant for transfer of triplet excitons from the light-emitting polymer to the triplet-accepting material may be selected so as to be greater than the rate constant for quenching of triplet excitons.

Light emitted from light-emitting compositions of the invention may include delayed fluorescence as described above, as well as fluorescence arising directly from recombination of holes and electrons on the light-emitting material ("prompt fluorescence").

The skilled person will be aware of methods to determine the presence of delayed fluorescence in light emitted from a light-emitting composition, for example by measuring light emission from a light-emitting composition following prompt fluorescence.

In the case of an OLED comprising the light-emitting composition, the delayed fluorescence can originate either from a TTA process, or from recombination of trapped charges with relatively long lifetimes. The TTA process can be distinguished from the trapped charge recombination process by applying a short spike of negative bias whilst measuring the intensity of the delayed fluorescence as described in detail by Popovic, Z. D. & Aziz, H. Delayed electroluminescence in small molecule based organic light emitting diodes: evidence for triplet-triplet annihilation and recombination centre mediated light generation mechanism. J. Appl. Phy. 98, 013510-5 (2005). If the negative bias has no lasting effect on the intensity of the delayed fluorescence, TTA is indicated (as opposed to non-prompt fluorescence arising from recombination of trapped charges where the delayed fluorescence is reduced after removal of the bias).

Triplet-Accepting Unit

The triplet-accepting unit as used may be a compound that is chemically unbound to, but physically mixed with, the light-emitting polymer and any other components of the light-emitting composition. Alternatively, the triplet-accepting unit may be bound, in particular covalently bound, to a component of the composition directly or through a spacer group.

In the case where the triplet-accepting unit is blended with the light-emitting polymer, the unit is preferably substituted with solubilising groups.

Exemplary triplet-accepting compounds include aromatic or heteroaromatic compounds comprising one or more mono- or polycyclic rings, and optionally including one or more alkenyl or alkynyl groups, for example polyaromatic hydrocarbons such as anthracenes and anthanthrenes and derivatives thereof; mono- or distyryl aryls and derivatives thereof such as distyrylbenzenes, distyrylbiphenyls, stilbenes, fulvenes, dibenzofulvenes, linear polyenes (from 2 to 6 alkenes) including cyclic polyenes such as cyclooctatetraene and further materials described in Handbook of Photochemistry, $2^{nd}$ Edition, Steven L Murov, Ian Carmichael and Gordon L Hug, the contents of which are incorporated herein by reference. Each said compound may optionally be substituted, for example substituted with alkyl groups. In one embodiment, the triplet-accepting unit does not comprise a polycyclic aromatic hydrocarbon unit comprising more than 12 sp² hybridised carbon atoms.
Exemplary mono- and di-styryl aryl compounds include the following:
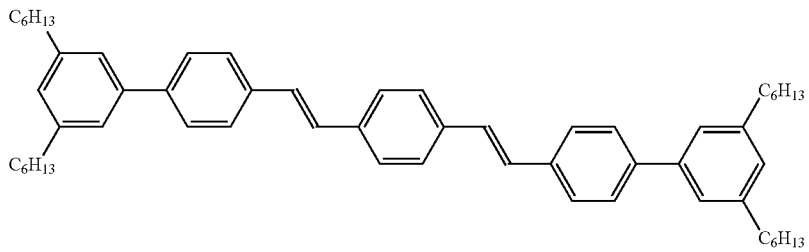
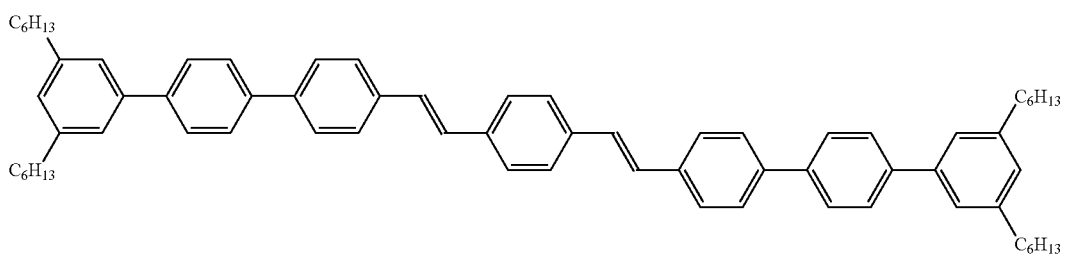
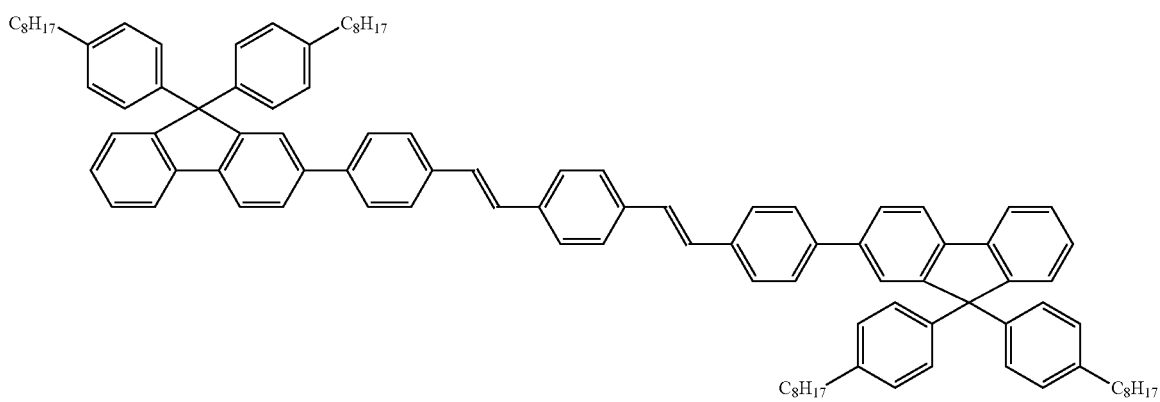
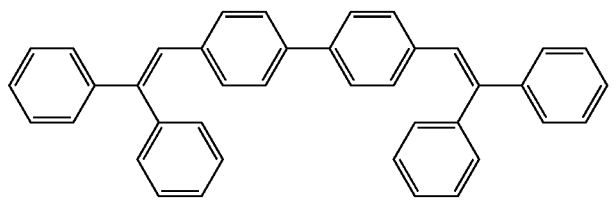
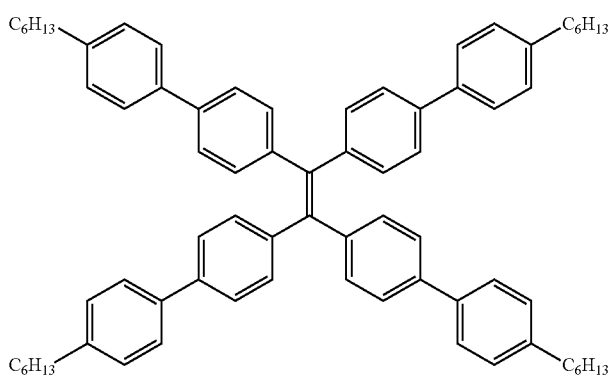

-continued
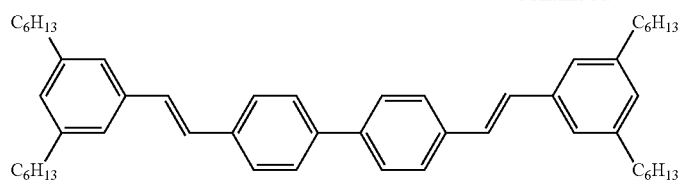
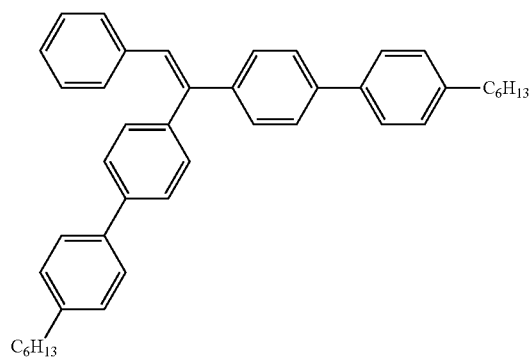
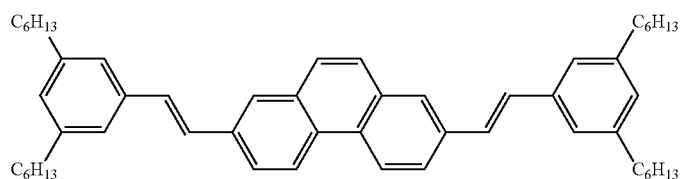
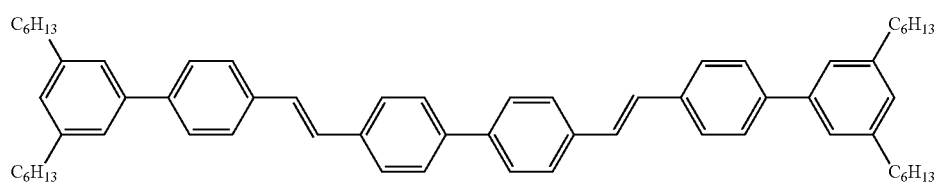
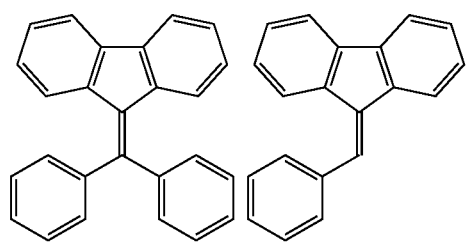

Exemplary anthanthrene compounds include the following:

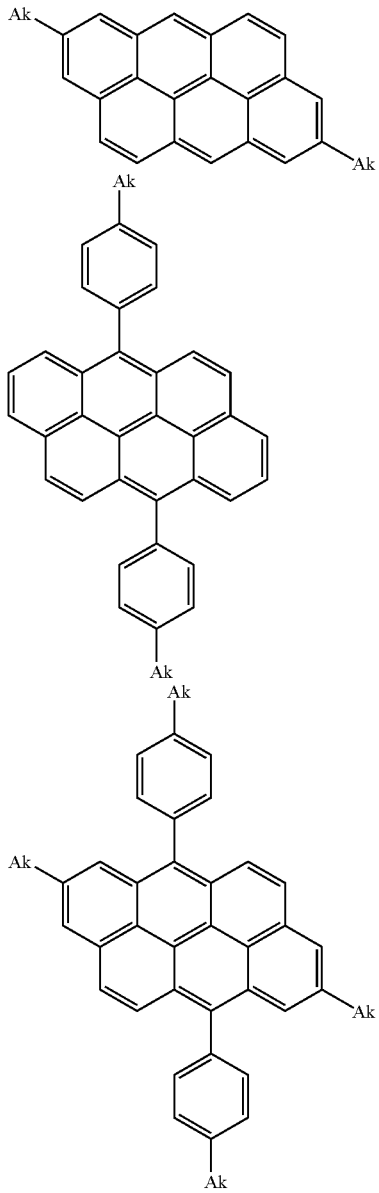

wherein Ak is alkyl, in particular branched or straight chain $C_{1-10}$ alkyl. Particularly preferred alkyl groups are n-butyl, t-butyl, n-hexyl and n-octyl.

The triplet-accepting unit may be a compound that is physically mixed with the light emitting polymer and any other components that may be present in the composition, or it may be bound to a the light-emitting composition or to one of these other components, where present. The other component or components may be may be, for example, one or more charge transporting materials such as a hole transporting or electron transporting material. In the case where the triplet-accepting unit is bound to the light-emitting polymer it may be provided as repeat units in the polymer main chain, one or more side groups pendant from the polymer main chain, or polymer end-groups.

The triplet-accepting unit may be bound into the main chain of a light-emitting polymer by polymerising a monomer comprising the triplet accepting repeat unit substituted with at least two polymerisable groups, such as leaving groups capable of participating in a metal-catalysed cross-coupling reaction (it will be appreciated that polymerisation of a monomer comprising more than two leaving groups will create a branch point in the polymer if more than two of the leaving groups react). Substitution of leaving groups on $sp^2$ carbon atoms of the triplet-accepting unit may be used for this purpose. Exemplary leaving groups include halogen and boronic acid or ester groups for use in Suzuki or Yamamoto polymerisation reactions, described in more detail below. The triplet-accepting unit may be bound to any repeat unit of the light-emitting polymer described below, for example to a light-emitting repeat unit, an electron-transporting repeat unit and/or a hole transporting repeat unit. In one embodiment, this polymer comprises a triplet-accepting repeat unit and an arylene co-repeat unit, for example a repeat unit of formula (IV) described below.

Exemplary repeat units include the following:

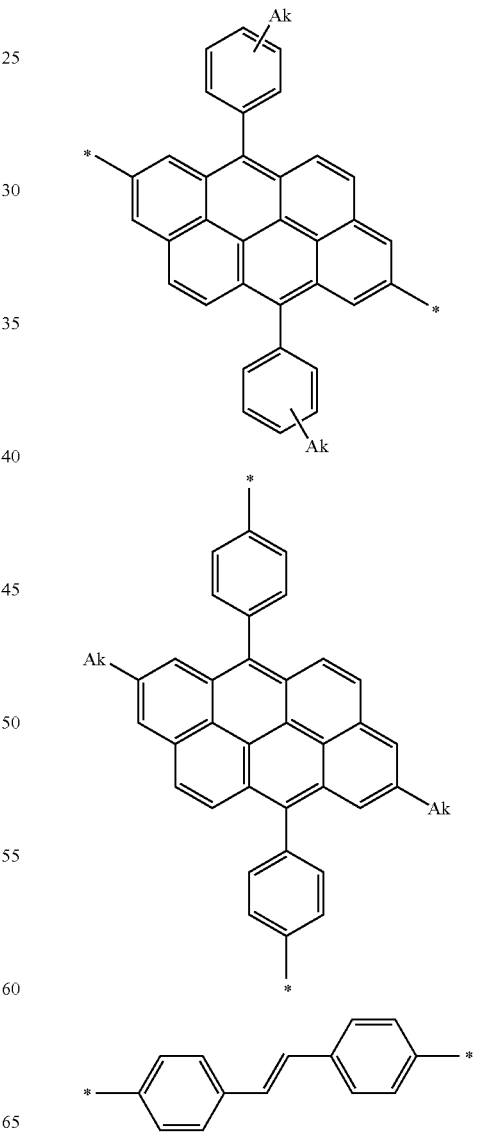

-continued

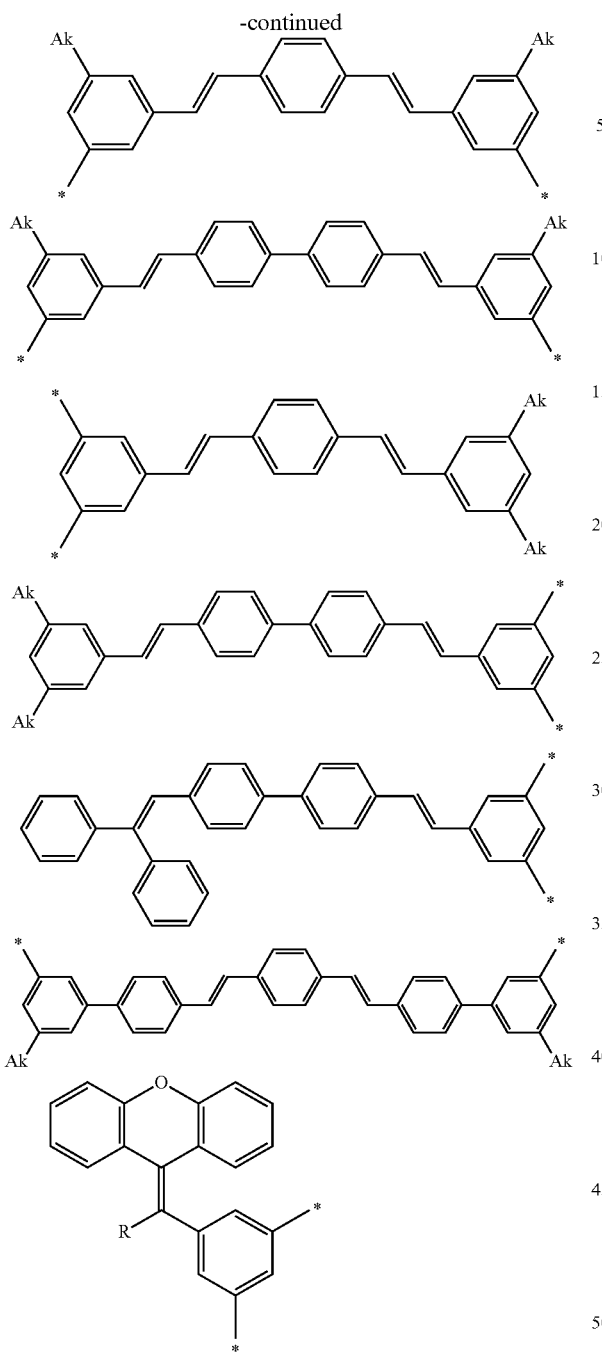

wherein * denotes the linking points for linking the repeat unit into the polymer chain, and Ak is alkyl, in particular branched or straight chain $C_{1-10}$ alkyl. Particularly preferred alkyl groups are n-butyl, t-butyl, n-hexyl and n-octyl. R is H or a substituent, optionally alkyl or optionally substituted aryl or heteroaryl, for example phenyl substituted with one or more alkyl groups.

The triplet-accepting unit may be provided as a side-group or end-group of a light-emitting polymer by reacting a compound substituted with one polymerisable group, such as a leaving group capable of participating in a metal-catalysed cross-coupling reaction, such as a halogen or boronic acid or ester, with a leaving group on the polymer.

Exemplary end-group units include the following:

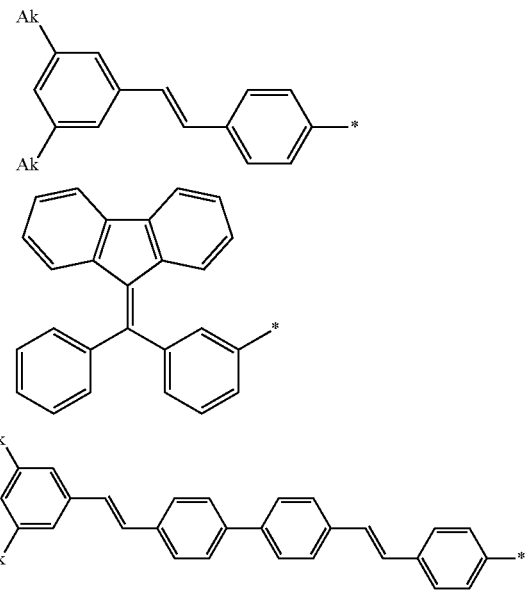

Alternatively, a side-group may be incorporated into a light-emitting polymer by providing it as a substituent of a monomer as illustrated below:

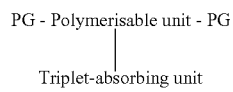

wherein PG represents a polymerisable group such as a leaving group as described above, or a polymerisable double bond.

Exemplary side-group monomers include the following:

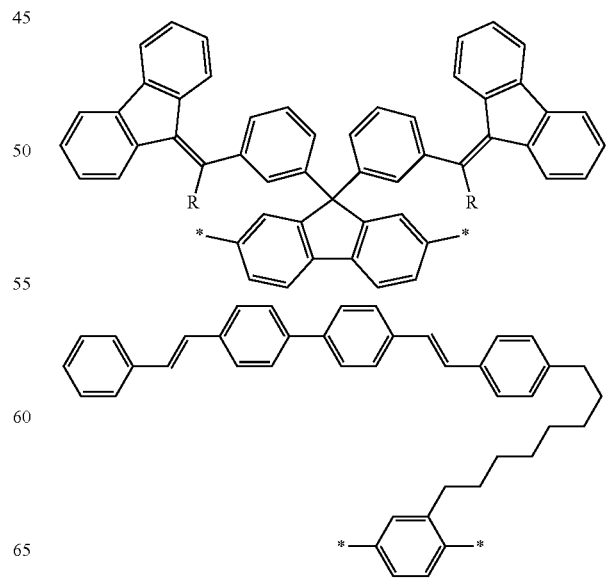

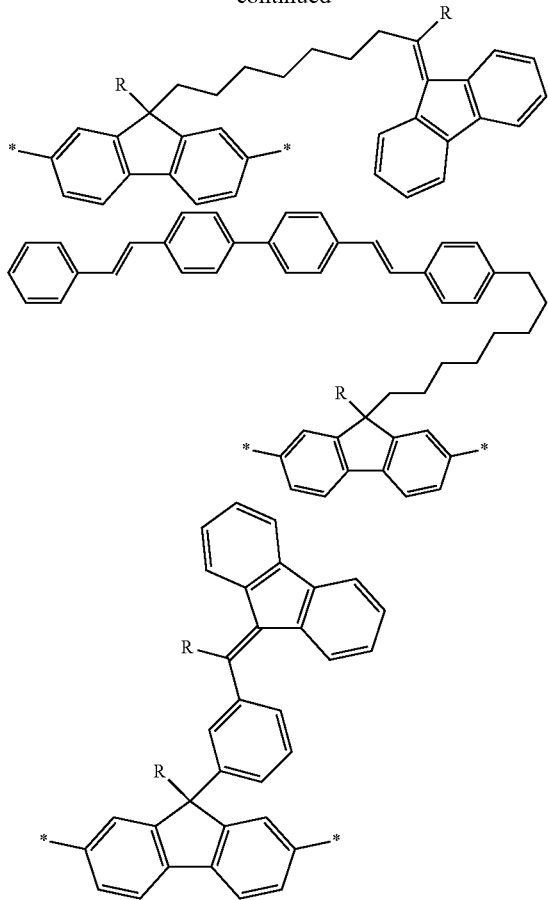

wherein * denotes the linking points for linking the repeat unit into the polymer chain, and R is alkyl, in particular branched or straight chain $C_{1-10}$ alkyl, heteroaryl or aryl, with optional alkyl, aryl or heteroaryl substituents.

In order to increase the probability of TTA and delayed fluorescence as described above, a plurality of triplet-accepting units may be provided in close proximity. For example, two such units may be provided in an optionally substituted unit having the general formula (II):

TAU-Spacer-TAU    (II)

wherein "TAU" represents a triplet accepting unit of formula (I) and the spacer is a conjugated or non-conjugated spacer group. The spacer group separates the two triplet-accepting TAU groups, and preferably separates their electronic characteristics (for example the HOMO and LUMO). Depending on the precise nature of the conjugation and orbital overlap, Sp could optionally comprise one or more arylene or heteroarylene groups such as substituted phenyl, biphenyl or fluorene. Alternatively, Sp could optionally comprise a non-conjugated linking group such as alkyl, or another molecular link that does not provide a conjugation path between the TAU groups.

The unit of formula (II) may be a separate compound physically mixed with the light-emitting polymer or it may be bound to the light-emitting polymer. In the case where the light-emitting polymer is a polymer, the unit of formula (II) may be bound as a main-chain repeat unit, a side group or an end-group as described above.

Alternatively or additionally, the triplet-accepting unit may be an oligomer or polymer, or a component of an oligomer or polymer, comprising a repeat structure of formula (IIb):

(TAU-Spacer)$_m$    (IIb)

wherein m is at least 2. This oligomer or polymer may be mixed with the light-emitting polymer or may be provided within the polymer backbone.

Although binding of the triplet-accepting unit to the light-emitting polymer is described above, it will be appreciated that the triplet-accepting unit may be bound to any other component of the composition, where present, in the same way. The concentration of the triplet-accepting unit is optionally at least 0.1 mol % or at least 1 mol %, for example in the range of 0.1-10 mol % or 1-10 mol % relative to the light emitting material. A higher concentration of the triplet-accepting material increases the probability of TTA.

In order to increase the probability of TTA, the lifetime of excited state triplets residing on the triplet accepting material is optionally at least 1 microsecond, optionally at least 10 microseconds, optionally at least 100 microseconds. The lifetime of a triplet exciton is its half-life, which may be measured by flash photolysis to measure monomolecular triplet lifetime as described in Handbook of Photochemistry, $2^{nd}$ Edition, Steven L Murov, Ian Carmichael and Gordon L Hug and references therein, the contents of which are incorporated herein by reference.

It will be appreciated that, unlike phosphorescent dopants, the triplet-accepting material does not provide an energetically favourable pathway for absorbed triplets to undergo radiative decay, and as a result substantially none of the energy of the triplet exciton absorbed by the triplet-accepting material is lost from the triplet-accepting material in the form of phosphorescent light emission from the triplet-accepting material.

The density of triplet excitons on a light-emitting material, for example on the polymer backbone of a conjugated light-emitting polymer, may be measured using quasi-continuous wave (quasi-cw) excited state absorption as described in more detail below.

Figure 4:
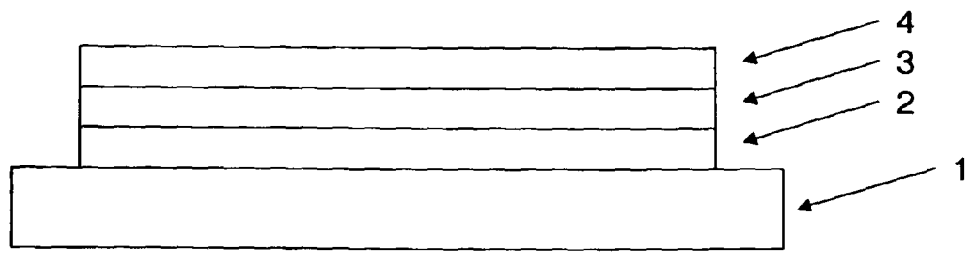
FIG. 4 illustrates an organic light-emitting device according to an example of the invention.

FIG. 4 illustrates the structure of an OLED according to an embodiment of the invention. The OLED comprises a transparent glass or plastic substrate 1, an anode 2, a cathode 4 and a light-emitting layer 3 provided between anode 2 and the cathode 4. Further layers may be located between anode 2 and the cathode, such as charge transporting, charge injecting or charge blocking layers.

Light Emitting Polymer

The light-emitting polymer may be a light-emitting homopolymer comprising light-emitting repeat units, or it may be a copolymer comprising light-emitting repeat units and further repeat units such as hole transporting and/or electron transporting repeat units as disclosed in, for example, WO 00/55927. Each repeat unit may be provided in a main chain or side chain of the polymer.

Suitable light-emitting polymers for use in layer 3 include poly(arylene vinylenes) such as poly(p-phenylene vinylenes) and polyarylenes such as: polyfluorenes, particularly 2,7-linked 9,9 dialkyl polyfluorenes or 2,7-linked 9,9 diaryl polyfluorenes; polyspirofluorenes, particularly 2,7-linked poly-9,9-spirofluorene; polyindenofluorenes, particularly 2,7-linked polyindenofluorenes; polyphenylenes, particularly alkyl or alkoxy substituted poly-1,4-phenylene. Such polymers as disclosed in, for example, Adv. Mater. 2000 12(23) 1737-1750 and references therein.

Light-emitting polymers preferably comprise a repeat unit selected from arylene repeat units as disclosed in, for example, Adv. Mater. 2000 12(23) 1737-1750 and references therein. Exemplary first repeat units include: 1,4-phenylene repeat units as disclosed in J. Appl. Phys. 1996, 79, 934; fluorene repeat units as disclosed in EP 0842208; indenofluorene repeat units as disclosed in, for example, Macromolecules 2000, 33(6), 2016-2020; and spirofluorene repeat units as disclosed in, for example EP 0707020. Each of these repeat units is optionally substituted. Examples of substituents include solubilising groups such as $C_{1-20}$ alkyl or alkoxy; electron withdrawing groups such as fluorine, nitro or cyano; and substituents for increasing glass transition temperature (Tg) of the polymer. Arylene repeat units, or a chain thereof, may provide electron-transporting functionality. For example, a chain of polyfluorenes may provide electron transporting functionality in the polymer.

Particularly preferred polymers comprise optionally substituted, 2,7-linked fluorenes, most preferably repeat units of formula IV:

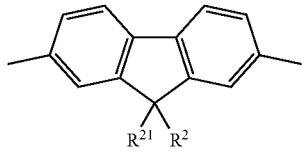

(IV)

wherein $R^1$ and $R^2$ are independently H or a substituent and wherein $R^1$ and $R^2$ may be linked to form a ring. $R^1$ and $R^2$ are preferably selected from the group consisting of hydrogen; optionally substituted alkyl wherein one or more non-adjacent C atoms may be replaced with O, S, N, C=O and —COO—; optionally substituted aryl or heteroaryl; and optionally substituted arylalkyl or heteroarylalkyl. More preferably, at least one of $R^1$ and $R^2$ comprises an optionally substituted alkyl, for example $C_1$-$C_{20}$ alkyl or aryl group.

"Aryl" and "heteroaryl" as used herein includes both fused and unfused aryl and heteroaryl groups respectively.

Optionally, fluorene repeat units are present in an amount of at least 50 mol %.

In the case where $R^1$ or $R^2$ comprises aryl or heteroaryl, a preferred aryl or heteroaryl group is phenyl, and preferred optional substituents include alkyl groups wherein one or more non-adjacent C atoms may be replaced with O, S, N, C=O and —COO—.

Optional substituents for the fluorene unit, other than substituents $R^1$ and $R^2$, are preferably selected from the group consisting of alkyl wherein one or more non-adjacent C atoms may be replaced with O, S, N, C=O and —COO—, optionally substituted aryl, optionally substituted heteroaryl, alkoxy, alkylthio, fluorine, cyano and arylalkyl.

Preferably, the polymer comprises an arylene repeat unit as described above and an arylamine repeat unit, in particular a repeat unit V:

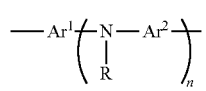

(V)

wherein $Ar^1$ and $Ar^2$ are optionally substituted aryl or heteroaryl groups, n is greater than or equal to 1, preferably 1 or 2, and R is H or a substituent, preferably a substituent. R is preferably alkyl or aryl or heteroaryl, most preferably aryl or heteroaryl. Any of the aryl or heteroaryl groups in the unit of formula 1, including the case where R is aryl or heteroaryl, may be substituted, and in one embodiment $Ar^1$, $Ar^2$ and R are each optionally substituted phenyl. Preferred substituents are selected from alkyl wherein one or more non-adjacent C atoms may be replaced with O, S, N, C=O and —COO—, optionally substituted aryl, optionally substituted heteroaryl, alkoxy, alkylthio, fluorine, cyano and arylalkyl. Preferred substituents include alkyl and alkoxy groups. Any of the aryl or heteroaryl groups in the repeat unit of Formula 1 may be linked by a direct bond or a divalent linking atom or group. Preferred divalent linking atoms and groups include O, S; substituted N; and substituted C.

Particularly preferred units satisfying Formula 1 include units of Formulae 1-3:

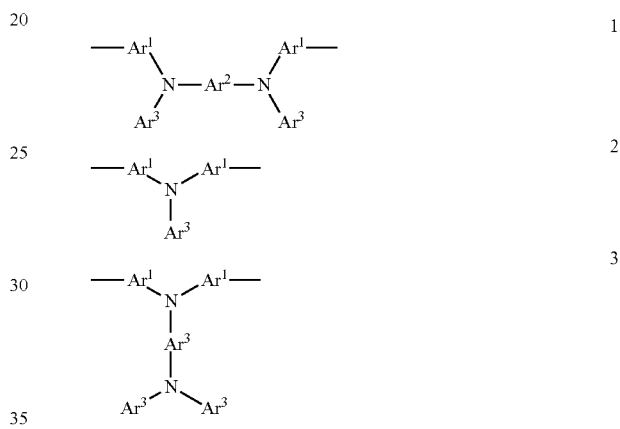

wherein $Ar^1$ and $Ar^2$ are as defined above; and $Ar^3$ is optionally substituted aryl or heteroaryl. Where present, preferred substituents for $Ar^3$ include alkyl and alkoxy groups.

The arylamine repeat units are preferably present in an amount up to 30 mol %, preferably up to 20 mol %. These percentages apply to the total number of arylamine units present in the polymer in the case where more than one type of repeat unit of formula V is used. Repeat units of formula (V) may provide one or more of hole transporting functionality and light-emitting functionality.

The polymer may comprise heteroarylene repeat units for charge transport or emission.

Binding a triplet-accepting unit to the light-emitting polymer may result in more efficient triplet acceptance as compared to mixing of a triplet-accepting material with the light-emitting polymer because this binding may provide intramolecular triplet acceptance pathways unavailable to a corresponding mixed system.

Moreover, binding may be beneficial for processing reasons. For example, if the triplet-accepting unit has low solubility then binding it to a soluble light-emitting polymer allows the triplet-accepting unit to be carried in solution by the light-emitting polymer, enabling device fabrication using solution processing techniques. Furthermore, if the triplet-accepting unit is a relatively volatile material, such as stilbene or a derivative thereof, then the risk of evaporation of the triplet accepting material during device fabrication is eliminated. This is a particular issue in the case of OLEDs formed using solution processing methods because light-emitting layers formed by deposition of a solution are typically heated as part of the device fabrication process (for example, to evaporate the solvent), which increases the likelihood of evaporation of volatile triplet-accepting units. Finally, binding the triplet accepting unit to the light-emitting polymer may prevent phase separation effects in solution-processed devices that may be detrimental to device performance.

Where the light-emitting polymer is a conjugated polymer comprising light-emitting repeat units and further repeat units, for example light-emitting amine repeat units of formula (V) and fluorene repeat units of formula (IV), conjugation of the triplet-accepting unit into the polymer main chain (for example by conjugation with fluorene repeat units) may reduce the $T_1$ energy level of the triplet-accepting unit, thus increasing the energetic favourability of triplet exciton transfer from the emitter unit to the triplet-accepting unit. This reduction in $T_1$ energy level of the triplet-accepting unit may also enable use of the triplet-accepting unit with light-emitting polymers with $T_1$ levels that are too low for use with a triplet-accepting unit that is not conjugated in this way.

Preferred methods for preparation of conjugated light-emitting polymers comprise a "metal insertion" wherein the metal atom of a metal complex catalyst is inserted between an aryl or heteroaryl group and a leaving group of a monomer. Exemplary metal insertion methods are Suzuki polymerisation as described in, for example, WO 00/53656 and Yamamoto polymerisation as described in, for example, T. Yamamoto, "Electrically Conducting And Thermally Stable π-Conjugated Poly(arylene)s Prepared by Organometallic Processes", Progress in Polymer Science 1993, 17, 1153-1205. In the case of Yamamoto polymerisation, a nickel complex catalyst is used; in the case of Suzuki polymerisation, a palladium complex catalyst is used.

For example, in the synthesis of a linear polymer by Yamamoto polymerisation, a monomer having two reactive halogen groups is used. Similarly, according to the method of Suzuki polymerisation, at least one reactive group is a boron derivative group such as a boronic acid or boronic ester and the other reactive group is a halogen. Preferred halogens are chlorine, bromine and iodine, most preferably bromine.

It will therefore be appreciated that repeat units illustrated throughout this application may be derived from a monomer carrying suitable leaving groups. Likewise, an end group or side group may be bound to the polymer by reaction of a suitable leaving group.

Suzuki polymerisation may be used to prepare regioregular, block and random copolymers. In particular, homopolymers or random copolymers may be prepared when one reactive group is a halogen and the other reactive group is a boron derivative group. Alternatively, block or regioregular, in particular AB, copolymers may be prepared when both reactive groups of a first monomer are boron and both reactive groups of a second monomer are halogen.

As alternatives to halides, other leaving groups capable of participating in metal insertion include groups include tosylate, mesylate and triflate.

Light-emitting layer 3 may consist of the light-emitting polymer and the triplet accepting unit alone, alone or may comprise these materials in combination with one or more further materials. In particular, the light-emitting polymer may be blended with hole and/or electron transporting materials or alternatively may be covalently bound to hole and/or electron transporting materials as disclosed in for example, WO 99/48160.

Light-emitting copolymers may comprise a light-emitting region and at least one of a hole transporting region and an electron transporting region as disclosed in, for example, WO 00/55927 and U.S. Pat. No. 6,353,083. If only one of a hole transporting region and electron transporting region is provided then the electroluminescent region may also provide the other of hole transport and electron transport functionality—for example, an amine unit as described above may provide both hole transport and light-emission functionality. A light-emitting copolymer comprising light-emitting repeat units and one or both of a hole transporting repeat units and electron transporting repeat units may provide said units in a polymer main-chain, as per U.S. Pat. No. 6,353,083, or in polymer side-groups pendant from the polymer backbone.

The light-emitting polymer may emit light of any colour provided that its $S_1$ and $T_1$ energy levels relative to the triplet-accepting unit are as described above, however the light-emitting polymer is preferably a blue light-emitting polymer, in particular a material having photoluminescent light emission with a peak wavelength in the range of from 400 to 500 nm, preferably 430 to 500 nm.

Light-emitting layer 3 may be patterned or unpatterned. A device comprising an unpatterned layer may be used an illumination source, for example. A white light emitting device is particularly suitable for this purpose. A device comprising a patterned layer may be, for example, an active matrix display or a passive matrix display. In the case of an active matrix display, a patterned electroluminescent layer is typically used in combination with a patterned anode layer and an unpatterned cathode. In the case of a passive matrix display, the anode layer is formed of parallel stripes of anode material, and parallel stripes of electroluminescent material and cathode material arranged perpendicular to the anode material wherein the stripes of electroluminescent material and cathode material are typically separated by stripes of insulating material ("cathode separators") formed by photolithography.

Hole Injection Layers

A conductive hole injection layer, which may be formed from a conductive organic or inorganic material, may be provided between the anode 2 and the electroluminescent layer 3 to assist hole injection from the anode into the layer or layers of semiconducting polymer. Examples of doped organic hole injection materials include optionally substituted, doped poly(ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. No. 5,723,873 and U.S. Pat. No. 5,798,170; and optionally substituted polythiophene or poly(thienothiophene). Examples of conductive inorganic materials include transition metal oxides such as VOx MoOx and RuOx as disclosed in Journal of Physics D: Applied Physics (1996), 29(11), 2750-2753.

Charge Transporting Layers

A hole transporting layer may be provided between the anode and the electroluminescent layer. Likewise, an electron transporting layer may be provided between the cathode and the electroluminescent layer.

Similarly, an electron blocking layer may be provided between the anode and the electroluminescent layer and a hole blocking layer may be provided between the cathode and the electroluminescent layer. Transporting and blocking layers may be used in combination. Depending on its HOMO and LUMO levels, a single layer may both transport one of holes and electrons and block the other of holes and electrons.

If present, a hole transporting layer located between anode 2 and electroluminescent layer 3 preferably has a HOMO level of less than or equal to 5.5 eV, more preferably around 4.8-5.5 eV. HOMO levels may be measured by cyclic voltammetry, for example.

If present, an electron transporting layer located between electroluminescent layer 3 and cathode 4 preferably has a LUMO level of around 3-3.5 eV. For example, a layer of a silicon monoxide or silicon dioxide or other thin dielectric layer having thickness in the range of 0.2-2 nm is provided between electroluminescent layer 3 and layer 4.

Polymers for use as charge transporting materials may comprise arylene units, such as fluorene units of formula (IV) and other units described above.

A hole-transporting polymer may comprise arylamine repeat units, in particular repeat units of formula (V), such as repeat units of formulae 1-3, described above. This polymer may be a homopolymer or it may be a copolymer comprising arylene repeat units in an amount up to 95 mol %, preferably up to 70 mol %. These percentages apply to the total number of arylamine units present in the polymer in the case where more than one type of repeat unit of formula (V) is used.

Charge transporting units may be provided in a polymer main-chain or polymer side-chain.

Cathode

Cathode 4 is selected from materials that have a workfunction allowing injection of electrons into the electroluminescent layer. Other factors influence the selection of the cathode such as the possibility of adverse interactions between the cathode and the electroluminescent material. The cathode may consist of a single material such as a layer of aluminium.

Alternatively, it may comprise a plurality of metals, for example a bilayer of a low workfunction material and a high workfunction material such as calcium and aluminium as disclosed in WO 98/10621; elemental barium as disclosed in WO 98/57381, Appl. Phys. Lett. 2002, 81(4), 634 and WO 02/84759; or a thin layer of metal compound, in particular an oxide or fluoride of an alkali or alkali earth metal, to assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a workfunction of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode will comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Encapsulation

Optical devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise a plastic as in U.S. Pat. No. 6,268,695 which discloses a substrate of alternating plastic and barrier layers or a laminate of thin glass and plastic as disclosed in EP 0949850.

The device is preferably encapsulated with an encapsulant (not shown) to prevent ingress of moisture and oxygen. Suitable encapsulants include a sheet of glass, films having suitable barrier properties such as silicon dioxide, silicon monoxide, silicon nitride or alternating stacks of polymer and dielectric as disclosed in, for example, WO 01/81649 or an airtight container as disclosed in, for example, WO 01/19142. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Solution Processing

Light-emitting layer 3 may be deposited by any process, including vacuum evaporation and deposition from a solution in a solvent. In the case where the light emitting layer comprises a polyarylene, such as a polyfluorene, suitable solvents for solution deposition include mono- or polyalkylbenzenes such as toluene and xylene. Particularly preferred solution deposition techniques including printing and coating techniques, preferably spin-coating and inkjet printing.

Spin-coating is particularly suitable for devices wherein patterning of the electroluminescent material is unnecessary—for example for lighting applications or simple monochrome segmented displays.

Inkjet printing is particularly suitable for high information content displays, in particular full colour displays. A device may be inkjet printed by providing a patterned layer over the first electrode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, roll printing and screen printing.

If multiple layers of an OLED are formed by solution processing then the skilled person will be aware of techniques to prevent intermixing of adjacent layers, for example by crosslinking of one layer before deposition of a subsequent layer or selection of materials for adjacent layers such that the material from which the first of these layers is formed is not soluble in the solvent used to deposit the second layer.

Monomer Example 1

A monomer for forming a triplet-quenching unit was prepared according to the following method:

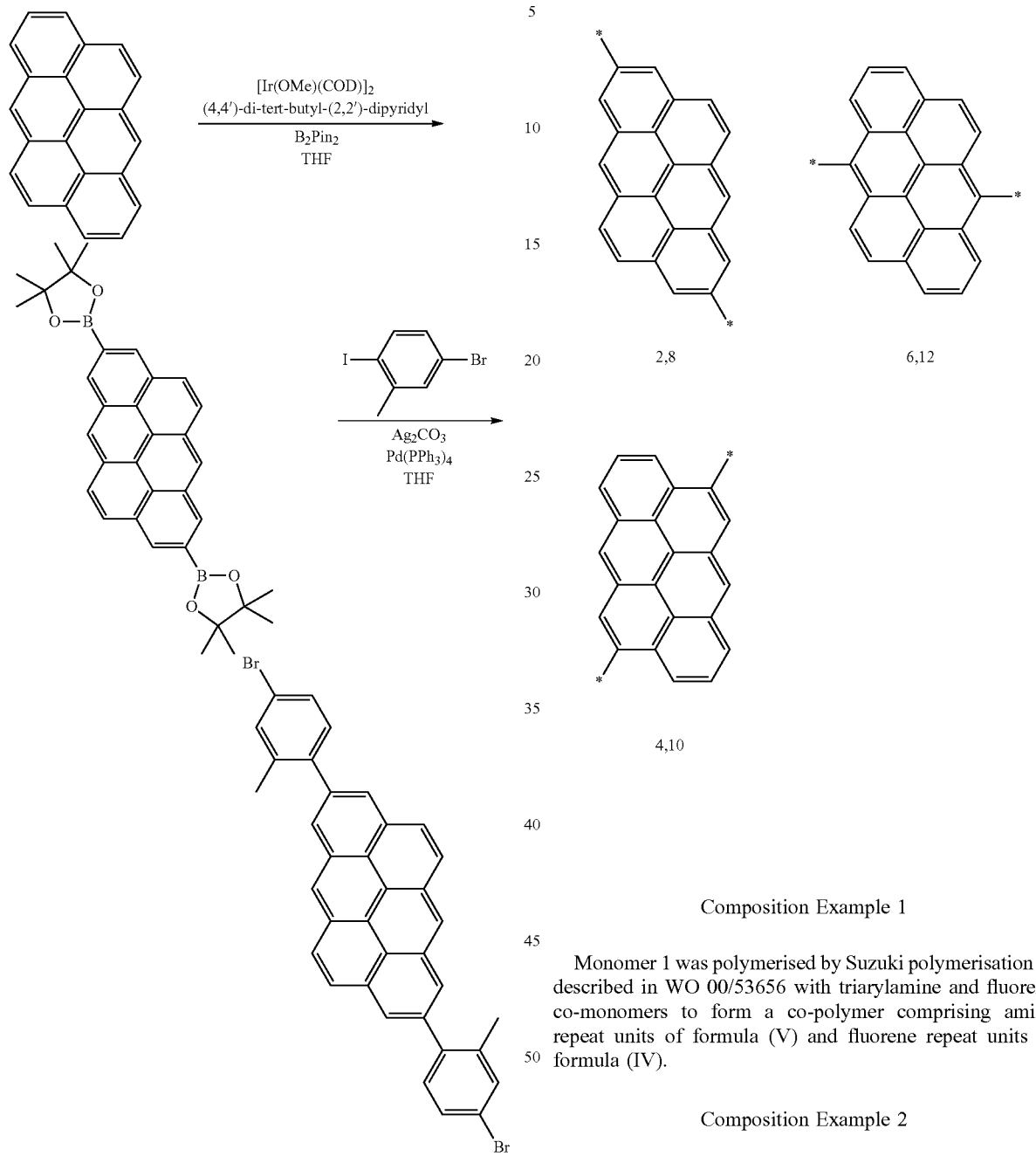

2,8

6,12

4,10

This synthesis illustrates substitution at the 2 and 8 positions. Analogous substitution may be provided at the 6,12 and/or 4,10-positions as illustrated below.

Monomer 1

Composition Example 1

Monomer 1 was polymerised by Suzuki polymerisation as described in WO 00/53656 with triarylamine and fluorene co-monomers to form a co-polymer comprising amine repeat units of formula (V) and fluorene repeat units of formula (IV).

Composition Example 2

A triplet-quenching material 11 was prepared according to the following method:

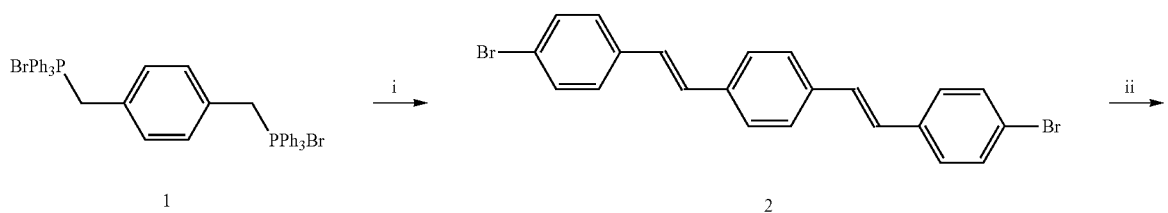

-continued
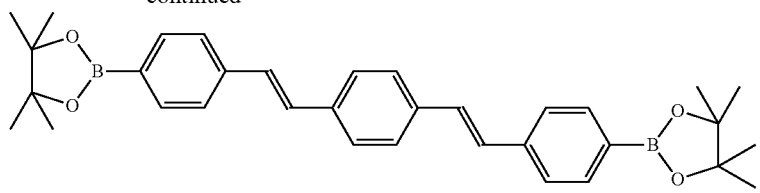
3
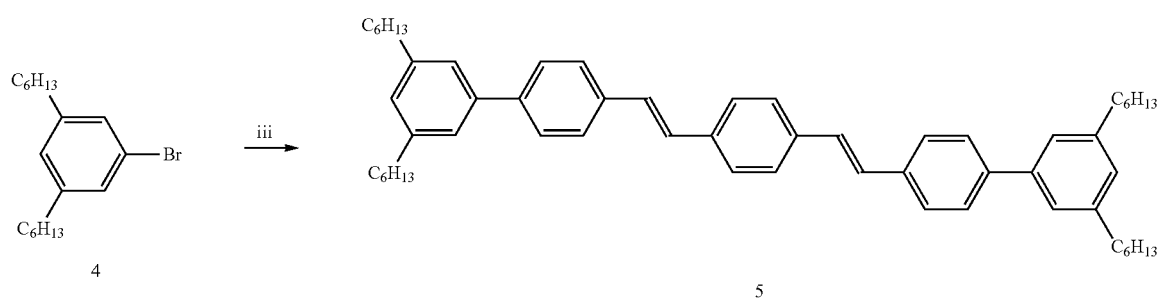
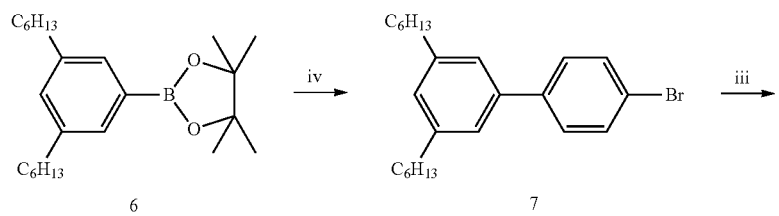
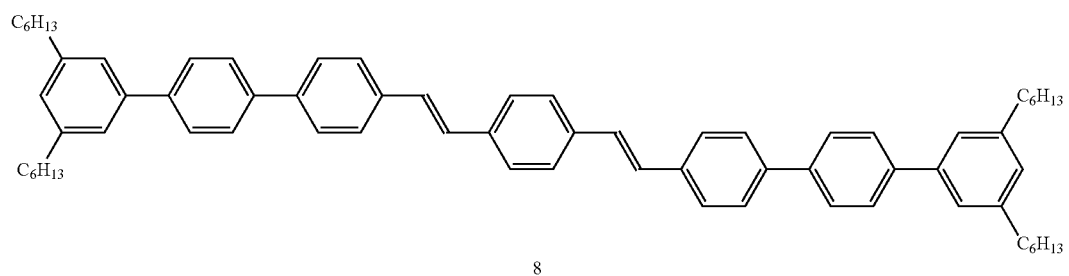
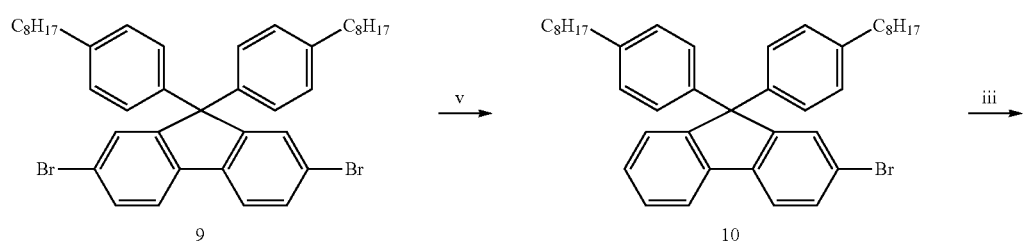

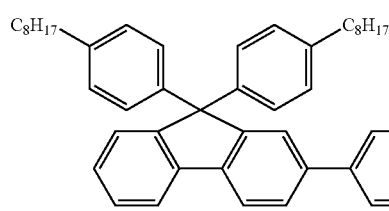
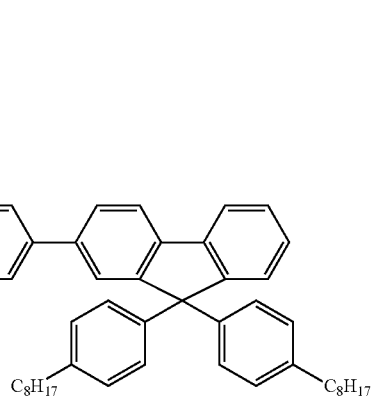

11 i. 4-bromobenzaldehyde, NaO$^t$Bu, THF, ii. BuLi, IPB, THF, iii. 3, Pd(PPh$_3$)$_2$Cl$_2$,, Et$_4$NOH, toluene, iv. 1-bromo-4-iodobenzene, Pd(PPh$_3$)$_4$, Ag$_2$CO$_3$, THF, v. BuLi, H$_2$O, THF

20

Compound 11 was mixed with a light-emitting polymer comprising fluorene repeat units of formula (IV) and light-emitting amine repeat units of formula (V).

Device Example 1

A device having the following structure was formed: ITO/HIL/HTL/EL/MF/Al
wherein ITO represents an indium-tin oxide anode; HIL is a 35 nm hole-injection layer; HTL is a 15 nm hole transport layer of a polymer comprising fluorene repeat units of formula (IV) and amine repeat units of formula (V); EL is an electroluminescent layer (70 nm) containing a light-emitting polymer comprising fluorene repeat units of formula (IV) and amine repeat units of formula (V) blended with a triplet accepting material; MF is a metal fluoride; and the bilayer of MF/Al forms a cathode for the device. The HIL, HTL and EL layers were deposited by spin-coating the composition from solution and evaporating the solvent.

Device Example 2

A device was formed as per Device Example 1, wherein HTL comprises the 50:50 mol copolymer F8-TFB (poly-(9, 9-dioctylfluorene-N-(4-(2-butyl)phenyl)-diphenylamine)) and EL comprises the 95:5 mol copolymer F8-PFB (poly-(9,9'-dioctylfluorene-co-bis-N,N'-(4-butylphenyl)-bis-N,N'-phenyl-1,4-phenylenediamine)) blended (1% mol ratio) with a triplet quenching additive DPVBi (4,4'-bis(2,2'diphenyl vinyl)-1,1'-biphenyl).

DPVBi has a triplet energy in the red-green portion of the spectrum (see Chen, P. et al. White organic light-emitting devices with a bipolar transport layer between blue fluorescent and orange phosphorescent emitting layers. *Appl. Phys. Lett.* 91, 023505-3 (2007); Schwartz, G., Fehse, K., Pfeiffer, M., Walzer, K. & Leo, K. Highly efficient white organic light emitting diodes comprising an interlayer to separate fluorescent and phosphorescent regions. *Applied Physics Letters* 89, 083509 (2006); and Romanovskii, Y. V. et al. Phosphorescence of pi-conjugated oligomers and polymers. *Phys. Rev. Lett.* 84, 1027-1030 (2000).

DPVBi also has a high singlet energy (3.2 eV) compared to the luminescent polymer so this molecule will accept the polymer triplets without affecting the emissive singlet states, this is confirmed by the observation that the incorporation of this small molecule into the polymer does not affect either the intensity or spectrum of the device photoluminescence.

(1)

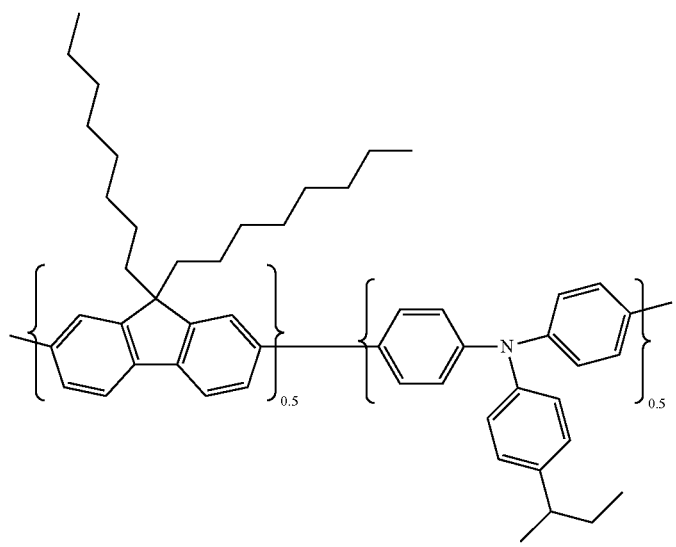

F8-TFB

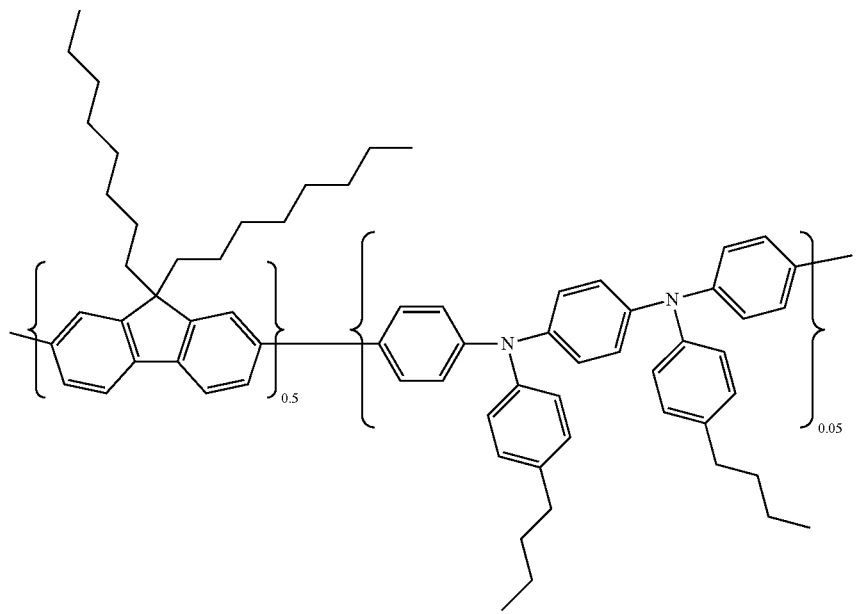

F8-PFB (2)

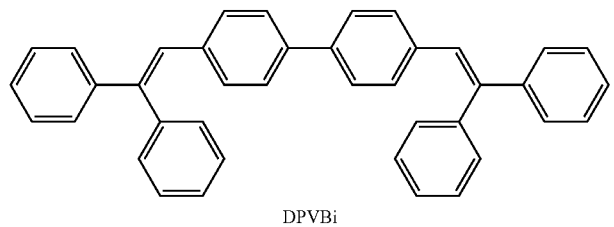

DPVBi (3)

The dynamics of the singlet and triplet excitons were studied using time resolved electroluminescence as well as quasi-cw and time resolved excited state absorption. The excited state absorption techniques have been described elsewhere (King, S., Rothe, C. & Monkman, A. Triplet build in and decay of isolated polyspirobifluorene chains in dilute solution. J. Chem. Phys. 121, 10803-10808 (2004), and Dhoot, A. S., Ginger, D. S., Beljonne, D., Shuai, Z. & Greenham, N. C. Triplet formation and decay in conjugated polymer devices. Chemical Physics Letters 360, 195-201 (2002)) and the triplet state of polyfluorenes has been well characterised with these techniques with a strong excited state absorption feature peaking at 780 nm attributed to the triplet state (King, S., Rothe, C. & Monkman, A. Triplet build in and decay of isolated polyspirobifluorene chains in dilute solution. J. Chem. Phys. 121, 10803-10808 (2004) and Rothe, C., King, S. M., Dias, F. & Monkman, A. P. Triplet exciton state and related phenomena in the beta-phase of poly(9,9-dioctyl)fluorene. Physical Review B 70, (2004)). Probes of the polyfluorene triplet population were performed at 780 nm, and the skilled person will understand how to modify this probe for other light-emitting materials based on the excited state absorption features of those materials.

Figure 5:
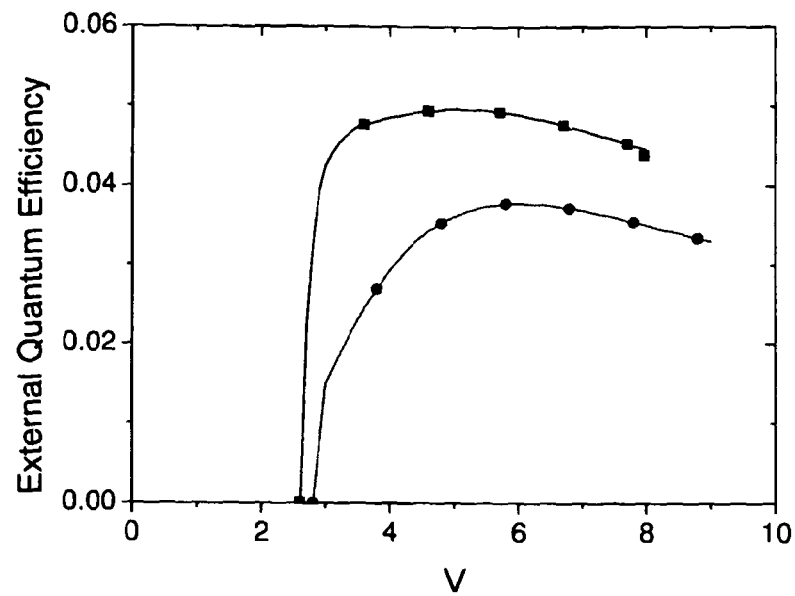
FIG. 5 is a graph of external quantum efficiency vs voltage for an exemplary device and a comparative device.

FIG. 5 shows the external quantum efficiency (EQE) of Device Example 2 (diamond), and that of a comparative device in which the triplet quenching additive is absent (square). The device with the triplet quenching additive shows a significant reduction in the peak EQE of approximately 20% at high voltage. The loss of efficiency occurs without any change to the electroluminescence spectrum of the device; therefore as would be expected from the singlet energy, the additive is neither quenching the singlet excitons nor taking part in the emission of the device. Without wishing to be bound by any theory, it is believed that the loss in efficiency is due to the removal of the TTA component caused by the quenching of the triplets from the light emitting polymer.

The density of triplet excitons on the polymer backbone is measured using quasi-cw excited state absorption as outlined above.

Figure 6:
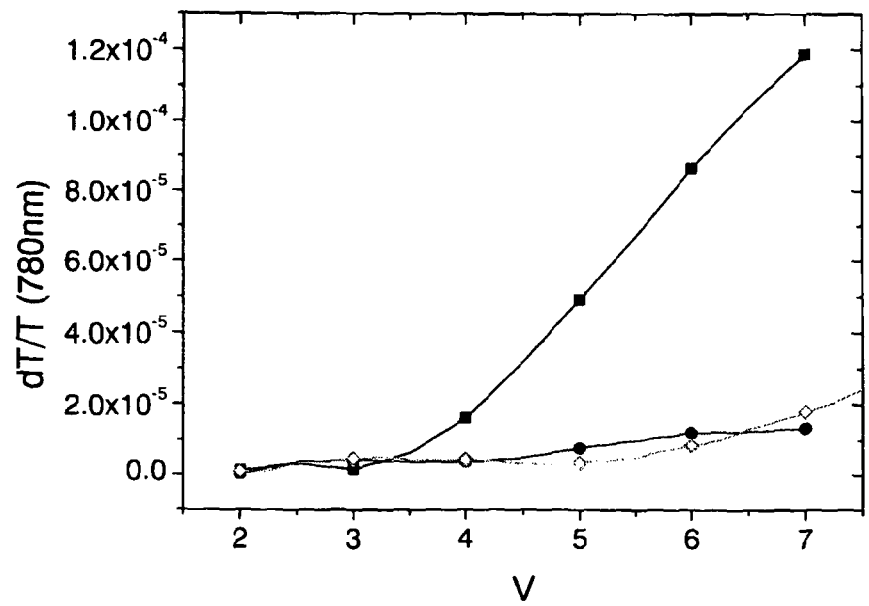
FIG. 6 is a graph illustrating triplet density for an exemplary device and a comparative device.

FIG. 6 shows the density of triplets on the polymer backbone both including (diamond) and excluding (square) the triplet quencher, in the device with the additive the density of triplets on the fluorene backbone is reduced by approximately a factor of 10, thus the additive is very efficient at quenching the triplets from the polymer at all device drive voltages. Literature values for the extinction coefficient of the triplet excited state absorption in conjugated polymers range[22] from $10^{-16}$-$10^{-15}$ cm$^2$ this gives a triplet density of $10^{16}$-$10^{17}$ cm$^{-3}$ in the standard device at typical drive currents of 50 mAcm$^{-2}$ and decay is dominated by their mutual bimolecular annihilation resulting in the production of emissive singlet excitons.

Figure 7:
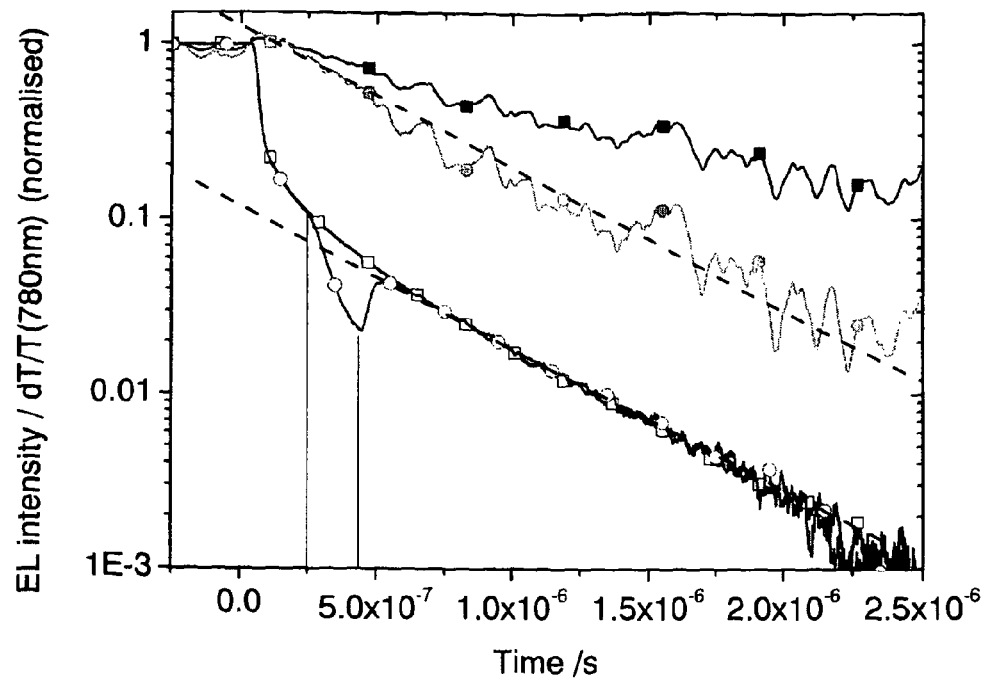
FIG. 7 is a graph of time resolved electroluminescence.

FIG. 7 shows the time resolved electroluminescence during the turn off of Device Example 2 compared with the time resolved transient triplet absorption and its square. The dotted lines are of the same slope. Also shown is the effect on the electroluminescence turn off when a reverse bias pulse of −10v 200 ns duration is applied to the device 250 ns after the device current is switched off.

After turn off of the current there is initially a rapid decay of the luminance on a similar timescale to the RC time constant of the device then a residual signal in the EL which accounts for about 30% of the total original electroluminescence and decays in a few microseconds. Generally slow transient emissions in OLEDs are ascribed to either the recombination of charges from deep traps or interfacial charge layers or TTA (see Kondakov, D. Y. Characterization of triplet-triplet annihilation in organic light-emitting diodes based on anthracene derivatives. *J. Appl. Phys.* 102, 114504-5 (2007), Sinha, S., Rothe, C., Guentner, R., Scherf, U. & Monkman, A. P. Electrophosphorescence and Delayed Electroluminescence from Pristine Polyfluorene Thin Film Devices at Low Temperature. *Physical Review Letters* 90, 127402 (2003), and Sinha, S., Monkman, A. P., Guntner, R. & Scherf, U. Space-charge-mediated delayed electroluminescence from polyfluorene thin films. *Appl. Phys. Lett.* 82, 4693-4695 (2003)).

In order to distinguish between the two mechanisms the same transient electroluminescence trace has been measured with the application of a 10v reverse bias pulse 100 ns after the turn off of the device current, this pulse will remove, or at least perturb significantly, any trapped charge contribution to the decay of the luminance. The data shows that although emission is quenched slightly during the reverse bias pulse due to the electric field quenching of the singlet excitons the decay of EL after the reverse bias pulse is unchanged compared to the standard decay shape. One can therefore conclude that that the recombination of trapped charge is not a significant contributor to the residual luminance signal (Popovic, Z. D. & Aziz, H. Delayed electroluminescence in small-molecule-based organic light-emitting diodes: Evidence for triplet-triplet annihilation and recombination-center-mediated light-generation mechanism. *J. Appl. Phys.* 98, 013510-5 (2005)). Moreover, comparing the shape of the residual luminescence with the triplet density (shown in FIG. 7) there are two observations, firstly that the timescale of the decay of the triplets is similar to the decay of the EL but more importantly the approximate slope of the decay of the residual luminance is very similar to the slope of the square of the triplet density. This observation is strong evidence that the residual decay of the EL is due to bimolecular triplet-triplet annihilation reactions resulting in emissive singlet excitons. It is valuable to note that the triplet exciton density is not significantly quenched by the application of a 10v reverse bias pulse because the triplets are considerably more stable than singlets to electric field due to their inherently greater exciton binding energy (Rothe, C., King, S. M. & Monkman, A. P. Electric-field-induced singlet and triplet exciton quenching in films of the conjugated polymer polyspirobifluorene. *Phys. Rev. B* 72, 085220 (2005) and Deussen, M., Scheidler, M. & Bassler, H. Electric-Field-Induced Photoluminescence Quenching in Thin-Film Light-Emitting-Diodes Based on Poly(Phenyl-P-Phenylene Vinylene). *Synth. Met.* 73, 123-129 (1995)).

Figure 8:
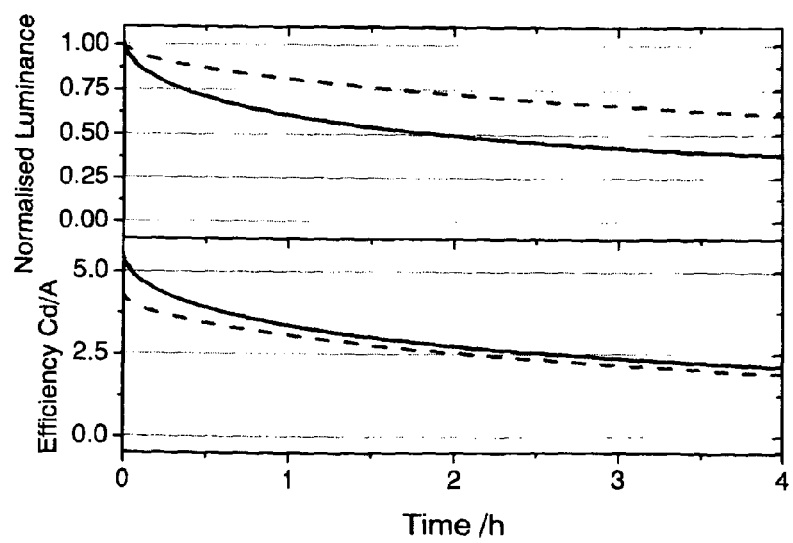
FIG. 8 is a graph of external quantum efficiency vs time for an exemplary device and a comparative device.

FIG. 8 shows the electroluminescence decay of a device both with (dotted line) and without (full line) the triplet quenching additive, the effect on the lifetime is clear, there is an improvement in T90 of approximately 5 times and an improvement of >3× to the final device lifetime. The lower panel of FIG. 5 which shows the efficiency of the devices during lifetest clearly shows that the extra efficiency boost from the TTA contribution is lost early on in the lifetest, after which the decay of the two devices is remarkably similar.

The cost to this gain in lifetime is the 20% drop in EQE from complete removal of TTA is easily outweighed by this stabilisation of the initial decay. In further arrangements, both high efficiency and lifetime may be achieved by utilising stable TTA as described above.

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A composition comprising a fluorescent light-emitting polymer mixed with a triplet-accepting polymer comprising a repeat unit of formula (IIb):

$$(\text{TAU-Spacer})_m \qquad (\text{IIb})$$

wherein TAU represents a triplet-accepting unit selected from the group consisting of: an anthracene TAU which is unsubstituted or substituted with one or more alkyl groups,

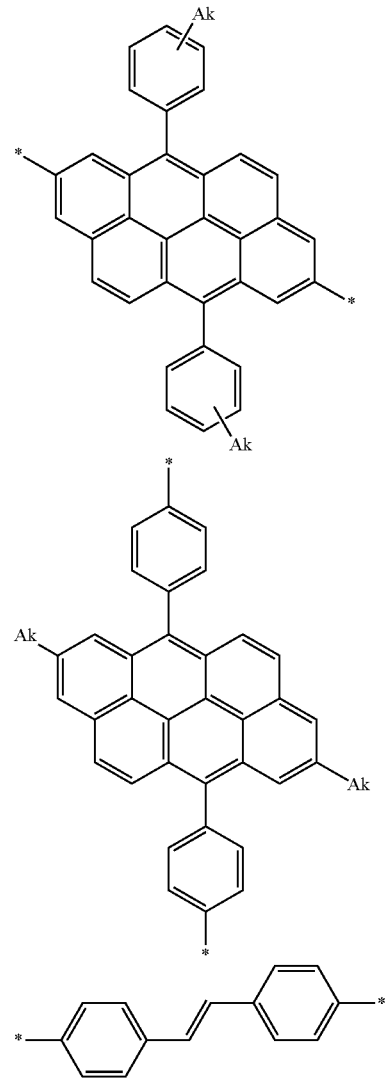

-continued

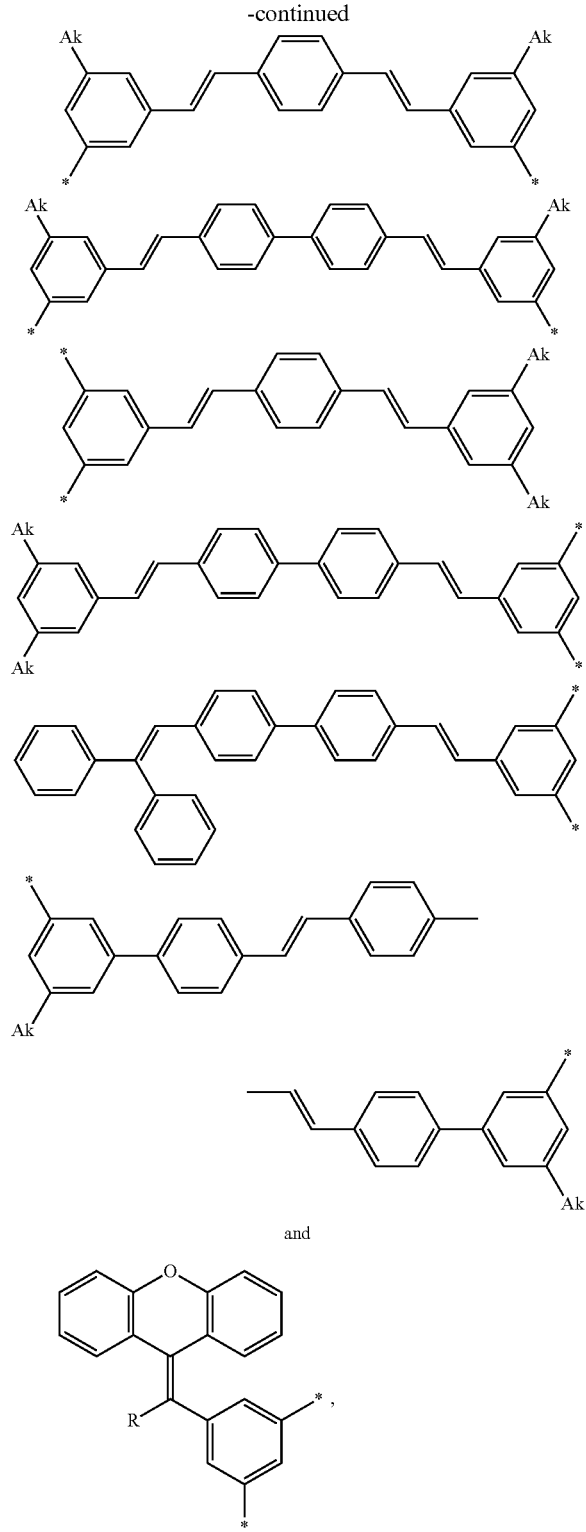

wherein * denotes the linking points for linking the repeat unit into the polymer chain, Ak is alkyl, and R is H or a substituent; Spacer is a spacer group selected from the group consisting of phenylene, biphenylene, and fluorene, and m is at least 2; wherein the triplet accepting polymer has a triplet energy level lower than that of the fluorescent light-emitting polymer.

2. A composition according to claim 1 wherein the composition comprises at least one of a hole transporting material and an electron transporting material.

3. A composition according to claim 1 wherein the light-emitting polymer comprises a light-emitting repeat unit and at least one of repeat units providing electron transport and repeat units providing hole transport.

4. A composition according to claim 1 wherein the light-emitting polymer comprises arylamine repeat units.

5. A composition according to claim 4 wherein the arylamine repeat units are units of formula (V):

$$-\!\!-\!\!Ar^1\!\!\left(\!\!-\!\!N\!\!-\!\!Ar^2\!\!-\!\!\right)_{\!\!n}$$
$$\phantom{xxxxxxx}|\phantom{xx}$$
$$\phantom{xxxxxxx}R\phantom{xx}$$

(V)

wherein $Ar^1$ and $Ar^2$ are optionally substituted aryl or heteroaryl groups, n is greater than or equal to 1, and R is H or a substituent.

6. A composition according to claim 5 wherein n is 1 or 2.

7. A composition according to claim 1 wherein the light-emitting polymer comprises aryl or heteroaryl repeat units.

8. A composition according to claim 7 wherein the light-emitting polymer comprises repeat units of formula (IV):

(IV)

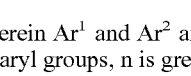

wherein $R^1$ and $R^2$ are independently H or a substituent, and $R^1$ and $R^2$ are optionally linked to form a ring.

9. A composition according to claim 1 wherein the composition has a photoluminescent light emission peak wavelength in the range of 400 to 500 nm.

10. A formulation comprising a solvent and a composition according to claim 1.

11. An organic light-emitting device comprising an anode, a cathode and a light-emitting layer between the anode and cathode, wherein the light-emitting layer comprises a composition according to claim 1.

12. A method of forming an organic light-emitting device according to claim 11, comprising the steps of:
depositing a formulation comprising a solvent and a composition comprising the fluorescent light-emitting polymer mixed with the triplet-accepting polymer; and
evaporating the solvent.

13. A method, comprising:
applying a voltage to an organic light-emitting device comprising an anode, a cathode, and a light-emitting layer between the anode and the cathode, wherein the light-emitting layer comprises a composition comprising a fluorescent light-emitting polymer mixed with a triplet-accepting polymer comprising a TAU of formula (IIb):

(TAU-Spacer)$_m$ (IIb)

wherein TAU represents a triplet-accepting unit selected from the group consisting of: an anthracene repeat unit which is unsubstituted or substituted with one or more alkyl groups,

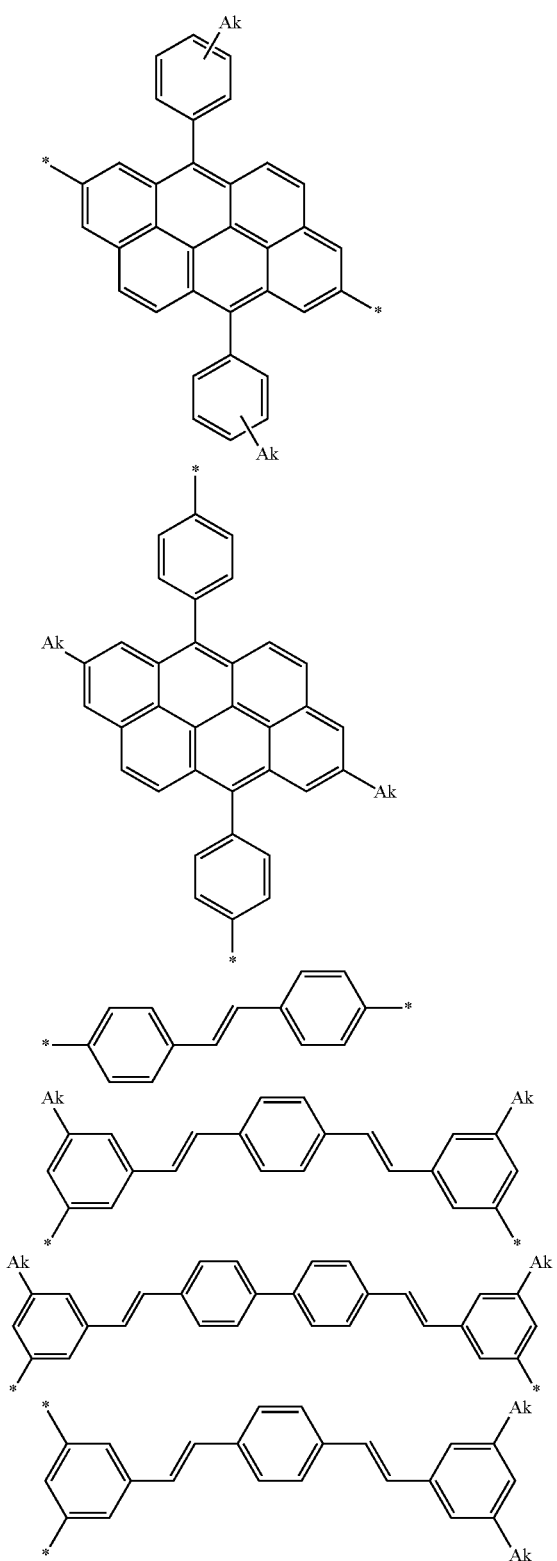

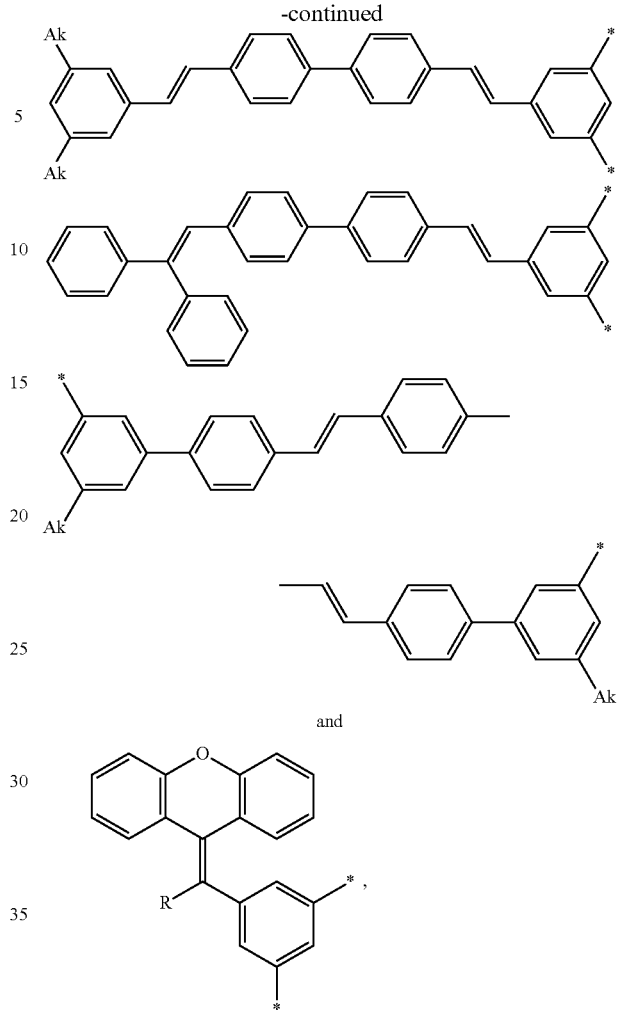

wherein * denotes the linking points for linking the repeat unit into the polymer chain, Ak is alkyl, and R is H or a substituent; Spacer is a spacer group selected from the group consisting of phenylene, biphenylene, and fluorene, and m is at least 2, wherein the triplet-accepting unit accepts triplet excitons generated by the light-emitting polymer.

14. A method according to claim 13 wherein the triplet-accepting unit quenches triplet excitons generated by the light-emitting polymer.

15. A method according to claim 13 wherein the triplet-accepting unit mediates triplet-triplet annihilation of triplet excitons transferred from the light-emitting polymer to the triplet-accepting unit.

16. The composition according to claim 1, wherein the composition is a fluorescent composition which emits substantially no phosphorescent light.

17. The composition according to claim 1, wherein delayed fluorescence is produced by the composition.

* * * * *